(12) United States Patent
Bates et al.

(10) Patent No.: US 6,682,505 B2
(45) Date of Patent: Jan. 27, 2004

(54) CATHETER FOR REMOVING EMBOLI FROM SAPHENOUS VEIN GRAFTS AND NATIVE CORONARY ARTERIES

(75) Inventors: Mark C. Bates, Charleston, WV (US); Michael Hogendijk, Palo Alto, CA (US); Ryan P. Boucher, San Francisco, CA (US)

(73) Assignee: Arteria Medical Science, Inc., San Francisco, CA (US)

( * ) Notice: Subject to any disclaimer, the term of this patent is extended or adjusted under 35 U.S.C. 154(b) by 0 days.

(21) Appl. No.: 09/909,729

(22) Filed: Jul. 19, 2001

(65) Prior Publication Data

US 2002/0107479 A1 Aug. 8, 2002

Related U.S. Application Data

(63) Continuation-in-part of application No. 09/418,727, filed on Oct. 15, 1999, now Pat. No. 6,423,032, which is a continuation-in-part of application No. 09/333,074, filed on Jun. 14, 1999, now Pat. No. 6,206,868.

(30) Foreign Application Priority Data

Mar. 12, 1999 (WO) ............................. PCT/US99/05469

(51) Int. Cl.[7] ............................................. A61M 29/00
(52) U.S. Cl. ................................ 604/96.01; 604/103.07
(58) Field of Search ...................... 604/96.01, 915–920; 606/191–194

(56) References Cited

U.S. PATENT DOCUMENTS

| | | | |
|---|---|---|---|
| 4,575,371 A | 3/1986 | Nordqvist et al. | |
| 4,781,681 A | 11/1988 | Sharrow et al. | |
| 4,794,928 A | 1/1989 | Kletschka | |
| 4,921,478 A | 5/1990 | Solano et al. | |
| 5,011,488 A | 4/1991 | Ginsburg | |
| 5,102,415 A | 4/1992 | Guenther et al. | |
| 5,284,473 A * | 2/1994 | Calabria ........................ | 604/53 |
| 5,549,626 A | 8/1996 | Miller et al. | |
| 5,584,803 A | 12/1996 | Stevens et al. | |
| 5,669,927 A | 9/1997 | Boebel et al. | |
| 5,749,858 A | 5/1998 | Cramer | |
| 5,766,151 A | 6/1998 | Valley et al. | |
| 5,794,629 A | 8/1998 | Frazee | |
| 5,833,650 A | 11/1998 | Imran | |
| 5,895,399 A | 4/1999 | Barbut et al. | |
| 5,916,193 A | 6/1999 | Stevens et al. | |
| 5,938,645 A | 8/1999 | Gordon | |
| 5,997,557 A | 12/1999 | Barbut et al. | |
| 6,013,085 A | 1/2000 | Howard | |
| 6,027,476 A | 2/2000 | Sterman et al. | |
| 6,029,671 A | 2/2000 | Stevens et al. | |
| 6,042,559 A | 3/2000 | Dobak, III | |
| 6,161,547 A | 12/2000 | Barbut | |
| 6,165,199 A | 12/2000 | Barbut | |
| 6,180,059 B1 | 1/2001 | Divino et al. | |
| 6,228,052 B1 | 5/2001 | Pohndorf | |
| 6,295,989 B1 | 10/2001 | Connors, III | |
| 6,398,773 B1 * | 6/2002 | Bagaoisan et al. ............ | 604/509 |
| 6,454,741 B1 * | 9/2002 | Muni et al. ............... | 604/96.01 |

FOREIGN PATENT DOCUMENTS

EP      0 427 429 A2    5/1991

* cited by examiner

*Primary Examiner*—Manuel Mendez
(74) *Attorney, Agent, or Firm*—Luce, Forward, Hamilton & Scripps; Nicole A. Pisano

(57) ABSTRACT

Methods and apparatus are provided for removing emboli generated during a surgical procedure comprising a catheter having proximal and distal ends, a lumen extending therethrough, an occlusive member affixed to the distal end, and at least one blood intake port disposed in a lateral surface of the catheter. The occlusive member preferably is disposed in a treatment vessel, and the blood intake port, when uncovered, permits a portion of the antegrade flow from a host vessel to be diverted into the lumen of the catheter. A pressure differential caused by the blood intake from the host vessel establishes a venturi-effect suitable for manipulating flow in the treatment vessel. The flow characteristics may be manipulated via the intake port to direct emboli into the lumen of the catheter for subsequent removal.

28 Claims, 15 Drawing Sheets

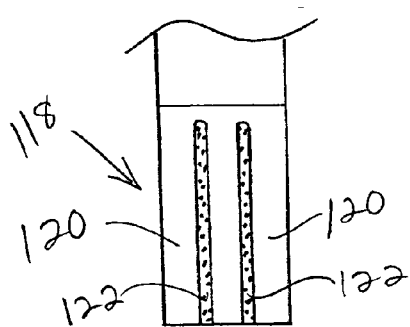
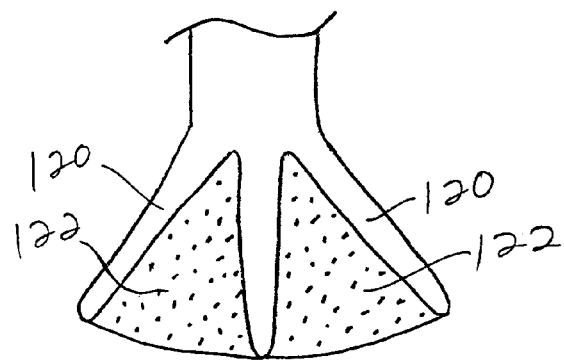
FIG. 6A    FIG. 6B
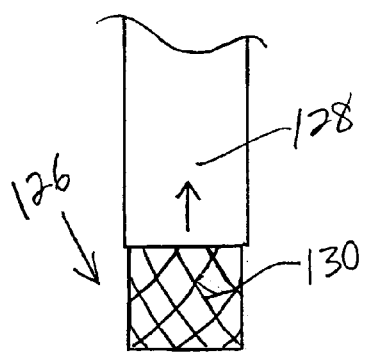
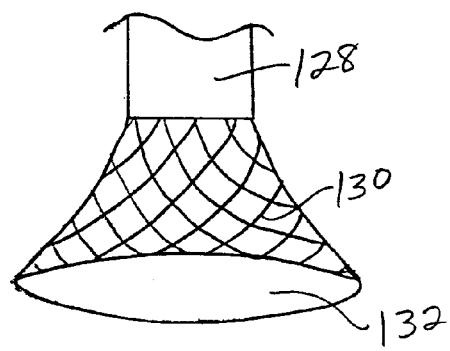
FIG. 7A    FIG. 7B
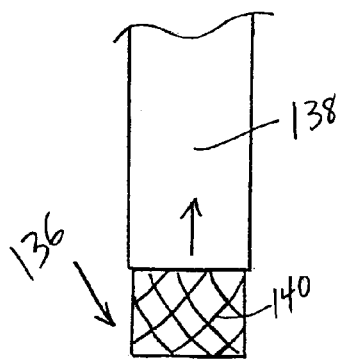
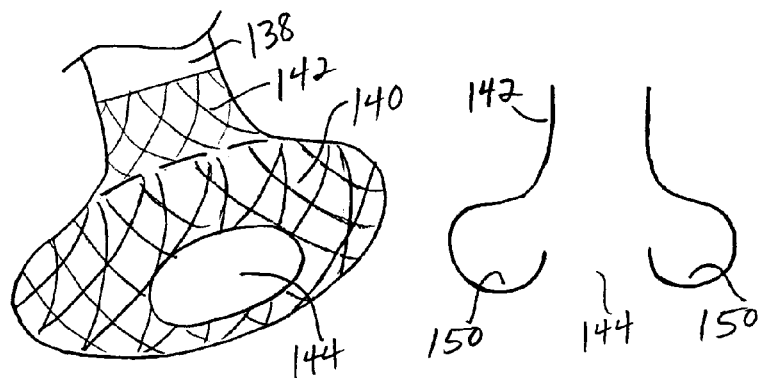
FIG. 8A    FIG. 8B    FIG. 8C

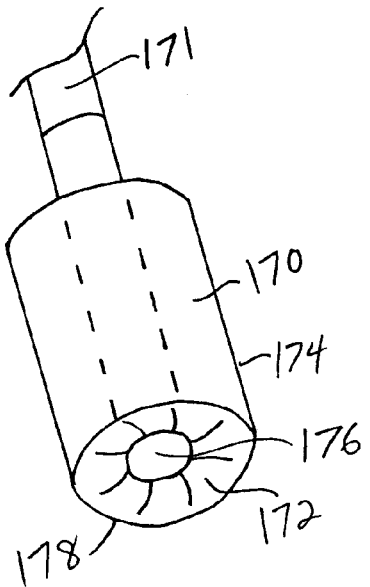 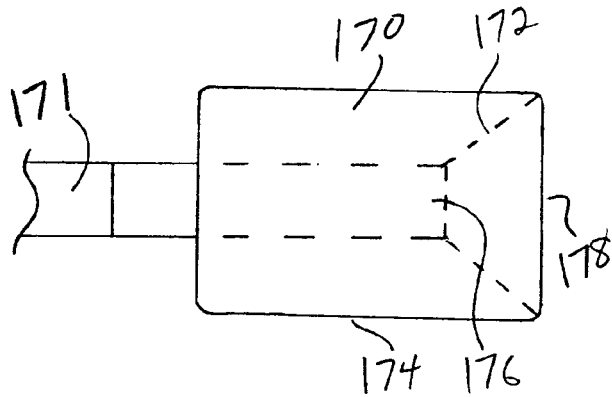
FIG. 9A  FIG. 9B
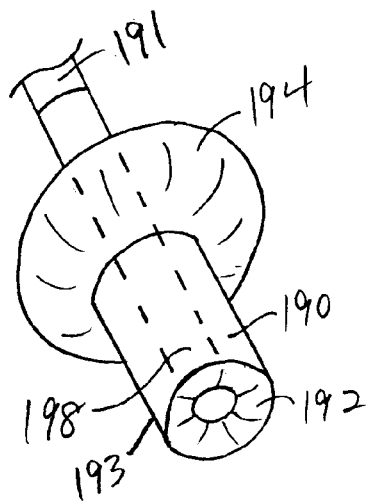 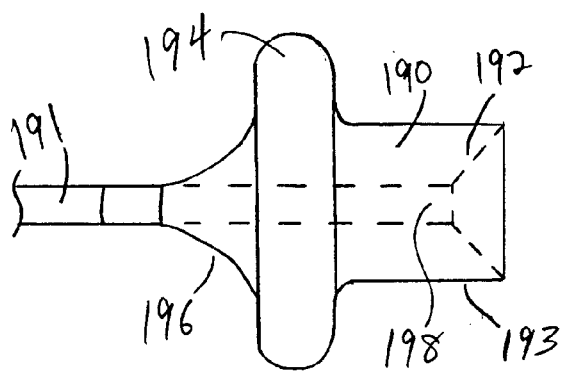
FIG. 10A  FIG. 10B

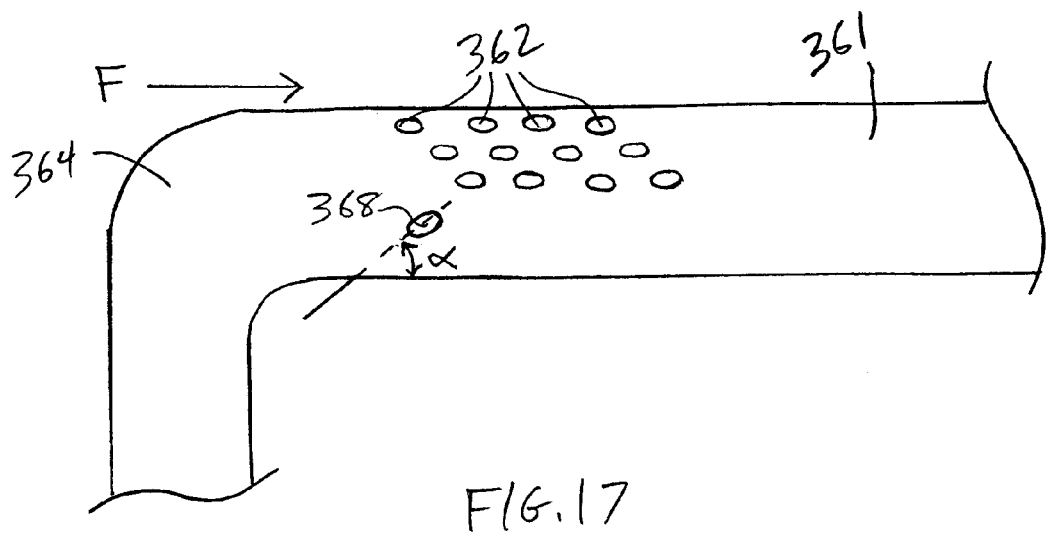
FIG. 17
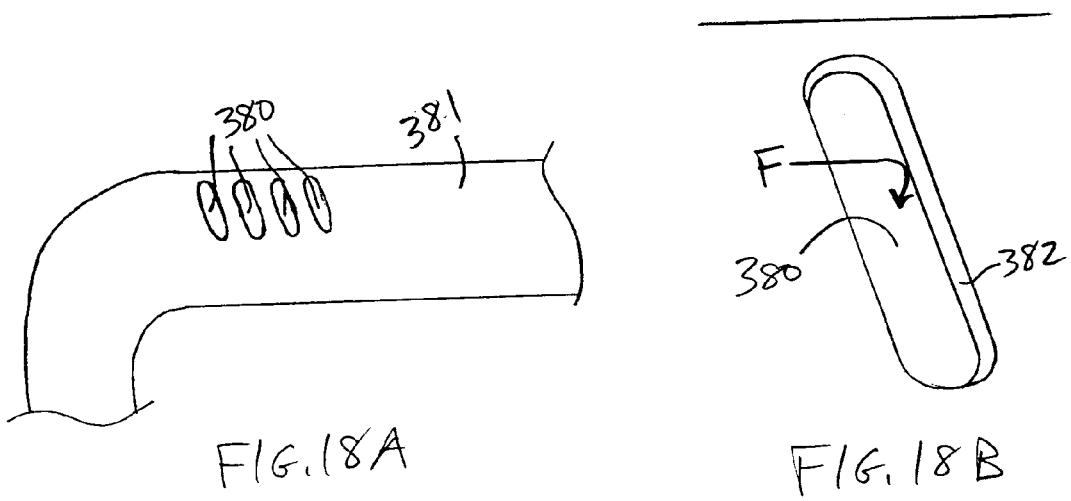
FIG. 18A
FIG. 18B
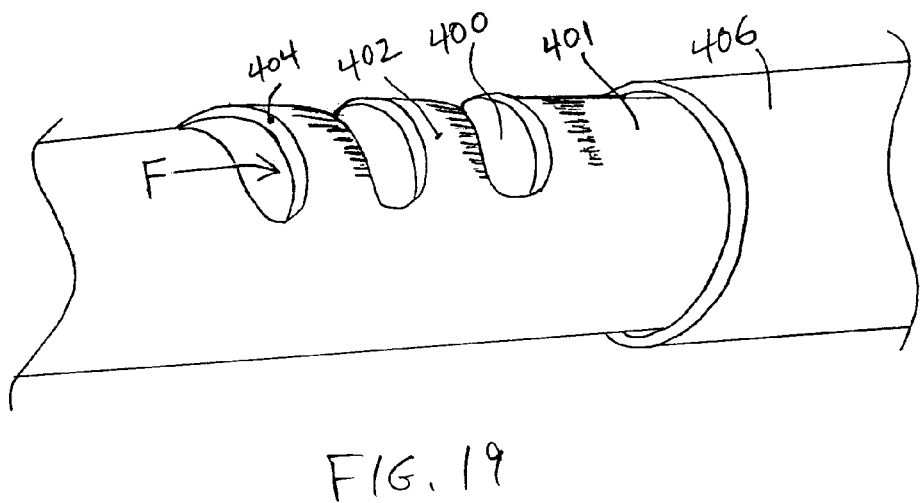
FIG. 19

CATHETER FOR REMOVING EMBOLI FROM SAPHENOUS VEIN GRAFTS AND NATIVE CORONARY ARTERIES

REFERENCE TO RELATED APPLICATIONS

The present application is a continuation-in-part of U.S. patent application Ser. No. 09/418,727, filed Oct. 15, 1999, now U.S. Pat. No. 6,423,032, which is a continuation-in-part of U.S. patent application Ser. No. 09/333,074, filed Jun. 14, 1999, which claims the benefit of priority of International Application PCT/US99/05469, filed Mar. 12, 1999.

FIELD OF THE INVENTION

The present invention relates to apparatus and methods for removal of emboli from within a vascular system. More particularly, the present invention provides a catheter having at least one blood intake port and an occlusive member through which venturi flow may be induced to remove emboli generated during an interventional procedure.

BACKGROUND OF THE INVENTION

Today there is a growing realization that steps must be taken to reduce the release of emboli during interventional procedures such as stenting, atherectomy and angioplasty. These procedures generally present a high risk for the release of embolic material that may occlude downstream portions of the vascular bed and cause ischemia. The resulting ischemia may pose a serious threat to the health or life of a patient if the blockage forms in a critical area, such as the heart, lungs, or brain.

Several previously known methods and apparatus employ an aspiration catheter for removal of the clots and/or emboli. U.S. Pat. No. 5,749,858 to Cramer describes apparatus for aspirating a blood clot by connecting a central catheter to a suction device. The Cramer device attempts to reduce problems associated with clogging of the catheter by providing a replacement catheter. U.S. Pat. No. 5,938,645 to Gordon describes a thrombectomy device for sweeping arteries and removing emboli using suction.

Previously known suction systems have several drawbacks. First, when using an external suction source, such as those described in the above-mentioned patents, it may be difficult to regulate the aspiration pressure at the treatment site. If the amount of suction is too low for the circumstances, then embolic particles may be incompletely removed, thus resulting in further occlusive events.

On the other hand, the application of too much suction may cause a vessel wall to collapse or dissect, resulting in significant damage to the vessel wall and potentially jeopardizing the patient's heath. In addition, an external suction device may induce a flow rate out of the vessel that cannot be sustained by the vessel wall for more than a few seconds, again potentially resulting in ischemia. Also, continuous use of an external suction device may result in excessive blood loss, requiring infusion of non-autologous blood. Finally, the use of an external suction device requires additional device complexity, including means to measure and regulate the applied suction.

Other methods for embolic removal have employed pressure gradients between the arterial system and the atmosphere to induce aspiration. For example, U.S. Pat. No. 4,921,478 to Solano et al. describes cerebral angioplasty methods and apparatus in which retrograde flow is induced through a catheter by leaving the proximal end of the catheter open to atmospheric pressure.

The foregoing solution to the problem of emboli removal, however, has several drawbacks which seem to have lead to abandonment of that approach. Chief among these problems is the inability of that system to generate flow reversal during placement of the guide wire and the angioplasty balloon across the stenosis. Because flow reversal does not occur until after deflation of the angioplasty balloon, there is a substantial risk that any emboli created during placement of the angioplasty balloon may travel too far downstream to be captured by the subsequent flow reversal, possibly causing further occlusive events.

In view of these drawbacks of previously known emboli removal systems, it would be desirable to provide apparatus and methods for removing emboli from within a blood vessel during an interventional procedure that reduces the volume of embolic particles released from the treatment site.

It also would be desirable to provide apparatus and methods for removing emboli that provide an appropriate level of retrograde flow at the treatment site, to direct dislodged particles into a catheter for efficient removal without damaging the treatment vessel.

It further would be desirable to provide apparatus and methods for removing emboli that utilize natural, physiologically regulated downstream flow from adjacent portions of the vascular system to achieve adequate retrograde flow in the treatment vessel.

It further would be desirable to provide apparatus and methods for removing emboli that eliminate the need for an external suction device to achieve retrograde flow, and to obviate the need to monitor and regulate such external suction device.

SUMMARY OF THE INVENTION

In view of the foregoing, it is an object of the present invention to provide a vascular device that overcomes disadvantages of previously known embolic removal systems.

It is another object of the present invention to provide apparatus and methods for removing emboli from within a blood vessel during an interventional procedure that reduces the volume of embolic particles that are released from the treatment site.

It is a further object of the present invention to provide apparatus and methods for removing emboli from a treatment site using an appropriate level of flow at the treatment site.

It is still a further object of the present invention to provide apparatus and methods for removing emboli that utilize natural, physiologically regulated downstream flow from adjacent portions of the vascular system to achieve adequate retrograde flow in the treatment vessel.

It is yet another object of the present invention to provide apparatus and methods for removing emboli that eliminate the need for an external suction device to achieve retrograde flow, and that obviate the need to monitor and regulate such external suction device.

These and other objects of the present invention are accomplished by providing a catheter having proximal and distal ends, and a lumen extending therethrough, an occlusive member at the distal end, and at least one blood intake port in a lateral surface of the catheter proximal of the occlusive member. In accordance with principles of the present invention, the catheter is configured to be percutaneously advanced in retrograde fashion through a host vessel until the distal end and occlusive member are positioned within the ostium of a treatment vessel or within the treatment vessel itself. The catheter may be used in conjunction with saphenous vein grafts, native coronary arteries, or other vessels. Upon deployment of the occlusive member, a portion of the antegrade flow through the host vessel will be diverted through the blood intake port, thereby inducing partial suction in the treatment vessel.

The diverted portion of the antegrade flow from the host vessel induces a controlled, physiologically regulated aspirating effect in the treatment vessel. The degree of suction induced in the treatment vessel may be controlled by adjusting the number or size of blood intake ports. A medical procedure then may be performed by inserting a therapeutic device, e.g., angioplasty catheter or embolectomy device, through the treatment lumen of the catheter to treat the lesion, while retrograde flow induced in the treatment vessel flushes blood containing emboli into the lumen of the catheter. The blood and emboli aspirated through the catheter may be filtered and then reperfused to the patient via a venous return system.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIGS. 5–11 show alternative embodiments of the distal occlusive member of the catheter;

DETAILED DESCRIPTION OF THE PREFERRED EMBODIMENTS

Figure 1:
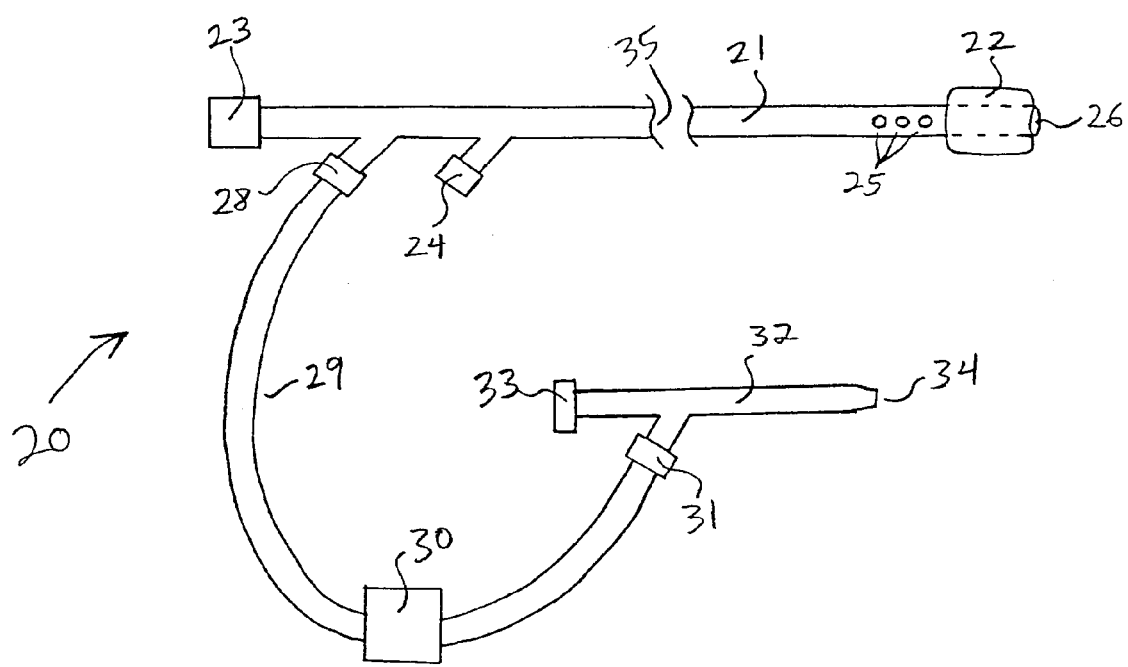
FIG. 1 is a schematic view of the apparatus of the present invention.

Referring now to FIG. 1, embolic protection apparatus 20 constructed in accordance with the principles of the present invention is described. Apparatus 20 comprises catheter 21, venous return line 32, tubing 29 and optional blood filter 30.

Catheter 21 comprises occlusive member 22, inlet port 26, hemostatic port 23, e.g., a Touhy-Borst connector, inflation port 24, blood outlet port 28, and at least one blood intake port 25. Lumen 35 communicates with inlet port 26, blood intake port 25, hemostatic port 23 and blood inlet port 28. As described hereinbelow, catheter 21 also preferably includes a mechanism for adjusting the size or number of blood intake ports 25. Tubing 29 couples blood outlet port 28 to optional filter 30 and blood inlet port 31 of venous return line 32. Hemostatic port 23 and the lumen of catheter 21 are sized to permit interventional devices, such as angioplasty balloon catheters, atherectomy devices and stent delivery systems, to be advanced through the lumen to the site of the occlusion.

Venous return line 32 includes hemostatic port 33, blood inlet port 31 and a lumen that communicates with ports 33 and 31 and outlet 34. Venous return line 32 may be constructed in a manner per se known for venous introducer catheters. Tubing 29 may comprise a suitable length of a biocompatible material, such as silicone. Alternatively, tubing 29 may be omitted and blood outlet port 28 of catheter 21 and blood inlet port 31 of venous return line 32 may be lengthened to engage either end of filter 30 or each other.

Figure 2:
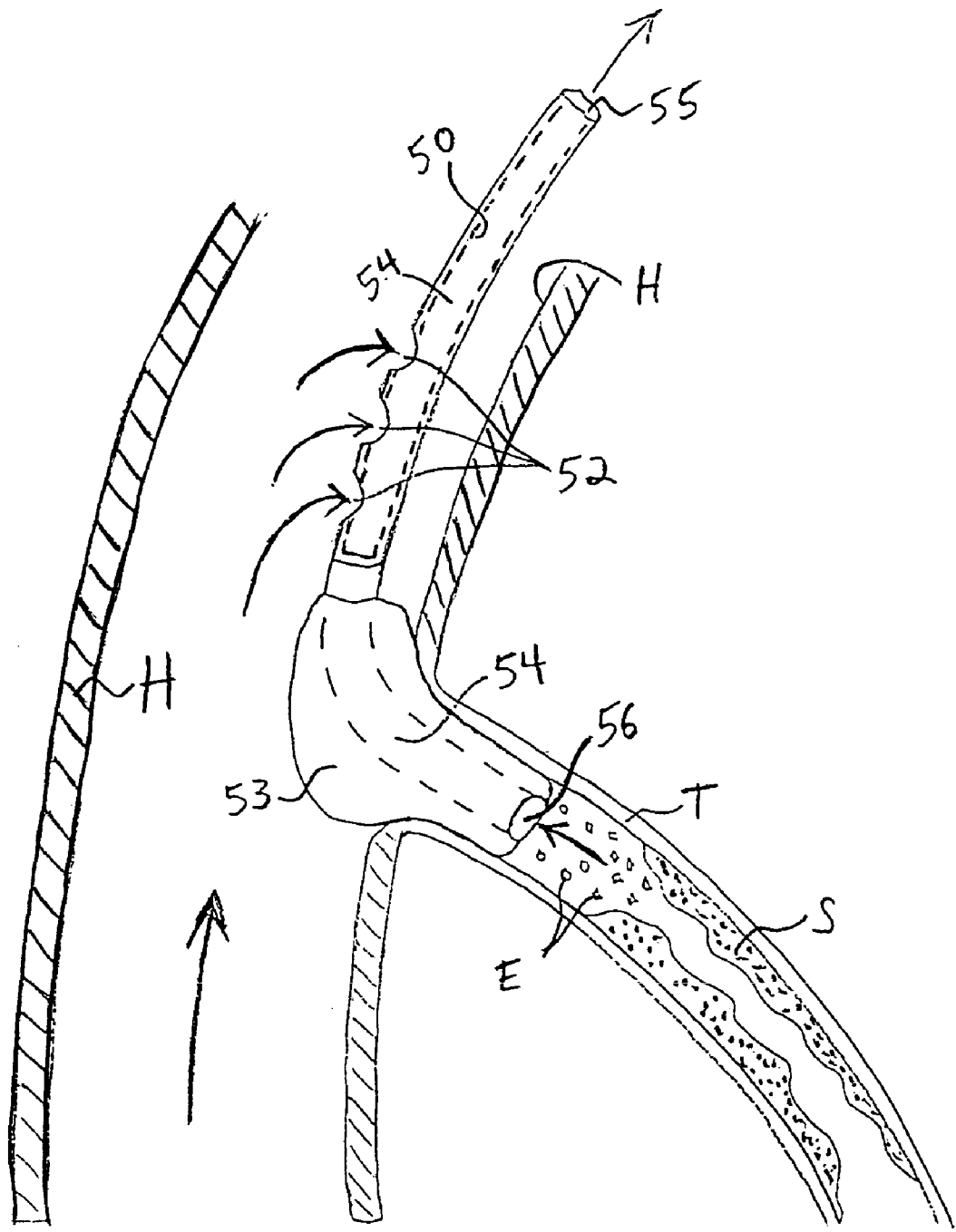
FIG. 2 is a schematic of the distal end of the apparatus in a fully deployed and actuated state within the body.

Referring now to FIG. 2, the features of catheter 21 best described in the context of using the catheter for embolic removal during an interventional procedure. First, the distal end of catheter 54 is introduced in a retrograde fashion into the body via host vessel H, such as the aorta, for example, by a percutaneous approach to the femoral artery. Inlet port 56 then may be positioned within the ostium of treatment vessel T proximal to lesion S, with occlusive member 53 disposed within the ostium of the treatment vessel and blood intake port 52 disposed in the host vessel.

Occlusive member 53 then is deployed to both anchor catheter 54 in place and to prevent blood entering through the ostium and into host vessel H. When occlusive member 54 is deployed, a portion of the antegrade flow through vessel H will be diverted into blood intake port 52. The flow from host vessel H enters blood intake port 52 and flows downstream within lumen 55 of catheter 54, in the directions indicated.

Because the volume of fluid flowing through host vessel H is greater than the volume of fluid flow within treatment vessel T, a venturi-type fluid effect is achieved, wherein fluid within treatment vessel T is induced to flow in a retrograde manner, as illustrated by the arrow in FIG. 2. With venturi-assisted flow established, a medical procedure, e.g., stenting, atherectomy, or angioplasty, then may be performed within treatment vessel T to disrupt lesion S. Disrupting lesion S may result in the formation of emboli E.

Advantageously, because retrograde flow already has been established within treatment vessel T due to the venturi effect, emboli E may be directed via the retrograde flow through removal port 56 and into catheter 54.

Unlike previously known systems that rely on external suction for aspiration, the present invention utilizes natural blood flow from a neighboring vessel. This adds a physiologically-limited degree of control, because the retrograde flow rate induced in treatment vessel T will be comparable to the flow rate of host vessel H, thereby potentially minimizing damage to the treatment vessel. Also, utilizing natural blood flow from an adjacent vessel alleviates reliance on an external suction monitoring device.

Figure 3A:
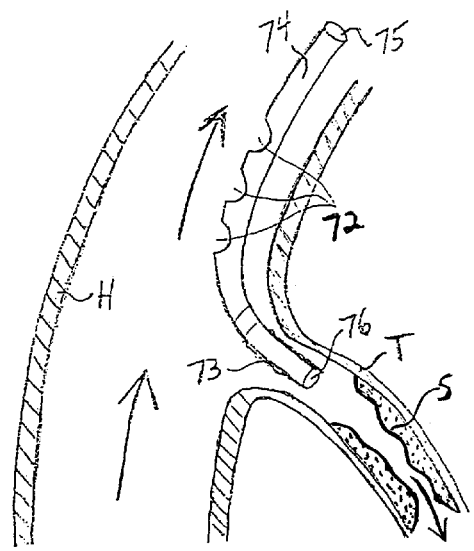
FIGS. 3A–3F depicts a method of using the apparatus of the present invention.

Referring to FIGS. 3A–3F, a method of using the apparatus of the present invention is described. In a first step, catheter 74 is introduced into host vessel H and positioned such that its distal end is introduced at least into the ostium of the treatment vessel T, as shown in FIG. 3A. The procedure preferably is performed with host vessel H being the aorta and treatment vessel T being either a saphenous vein graft or native coronary artery. Occlusive member 73 at the distal end of catheter 74 is not yet deployed. At the distal end of catheter 74, removal port 76 is positioned proximal to stenotic lesion S, as shown.

Figure 3B:
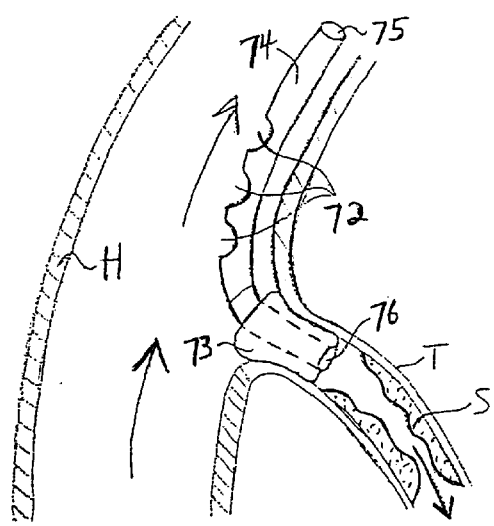

Referring now to FIG. 3B, occlusive member 73 is illustrated as having an inflatable balloon configuration. In alternative embodiments described hereinbelow, occlusive member 73 may be mechanically deployed or have various other balloon configurations. For the inflatable balloon configuration depicted in FIG. 3B, occlusive member 73 is inflated via inflation port 24. In accordance with manufacturing techniques which are known in the art, inflatable occlusive member 73 comprises a compliant material, such as polyurethane, latex or polyisoprene, and is affixed to distal end of catheter 74, for example, by gluing or a melt-bond.

Upon inflation, occlusive member 73 forms a seal between host vessel H and treatment vessel T such that fluid does not flow in an antegrade direction around the occlusive member and into the ostium of the treatment vessel. Accordingly, removal port 76 is exposed exclusively to flow within treatment vessel T. Additionally, occlusive member 73 stabilizes the apparatus upon inflation by acting as an anchor, and provides a funneled entry into removal port 76.

Blood intake port 72 may comprise one port or a plurality of ports, and may be provided in various configurations described hereinbelow. It may be appreciated that illustrations depicting a plurality of intake ports and textual references referring to a plurality of ports may actually represent one intake port, and vice versa.

Blood intake port 72 is initially closed such that lumen 75 interacts solely with flow from treatment vessel T. At this time, contrast, cardioplegia, therapeutic drugs or other agents may be administered to the treatment vessel via lumen 75. The agents may be injected into lumen 75, for example, using a syringe attached to a proximal hub assembly.

Figure 3C:
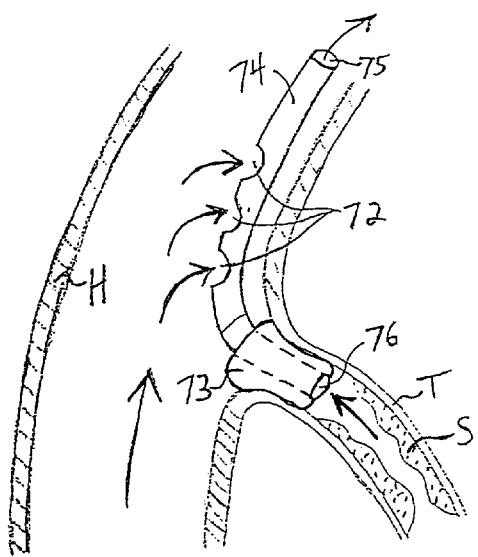

Referring to FIG. 3C, blood intake port 72 is uncovered and exposed to downstream flow from within host vessel H. Fluid from host vessel H enters blood intake port 72, as shown, and flows downstream within lumen 75 of catheter 74.

Given that the volume of fluid flow created downstream, i.e., proximal to occluding member 73, is greater than the volume of fluid flow within treatment vessel T, a venturi-type fluid effect will be established whereby fluid within treatment vessel T is induced to flow in a retrograde direction in the treatment vessel. Subsequently, fluid in treatment vessel T enters removal port 76 and travels downstream within lumen 75 toward the proximal end of catheter 74.

Venous return line 32 of FIG. 1 then may be introduced into the patient's femoral vein, either percutaneously or via a surgical cut-down. Filter 30 is coupled between blood outlet port 28 of catheter 21 and blood inlet port 31 of venous return line 32 using tubing 29, and any air is removed from the line. Blood traveling downstream within lumen 75 passes through blood outlet port 28 and back into the patient's femoral vein via venous return line 32, thus reducing the amount of blood lost during the procedure and allowing autologous blood to be recycled.

Figure 3D:
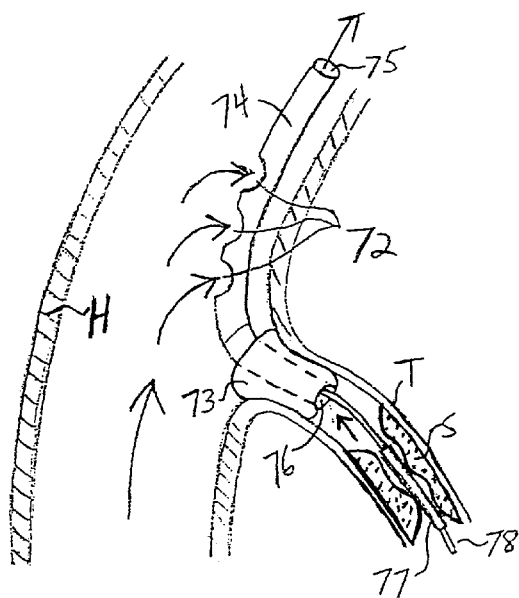
Figure 3E:
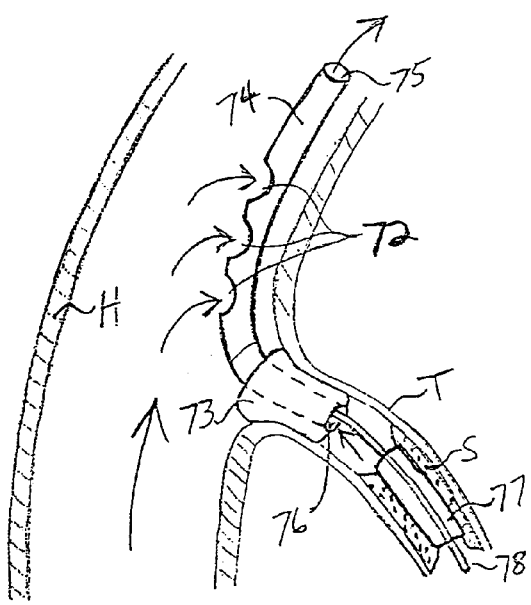

Referring to FIG. 3D, with occlusive member 73 deployed and a retrograde flow established in the treatment vessel, an interventional instrument, e.g., conventional angioplasty balloon catheter 78 having balloon 77, is loaded through hemostatic port 23 and lumen 75, then is positioned within lesion S. Hemostatic port 23 is closed, and instrument 78 is actuated to restore vessel patency, as shown in FIG. 3E.

Figure 3F:
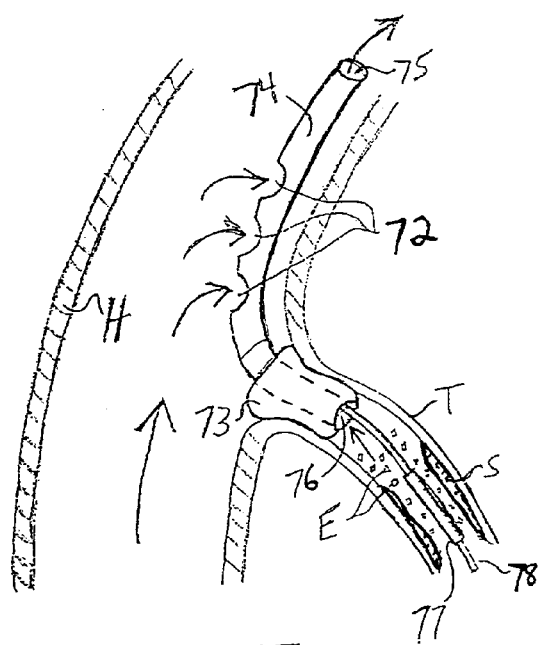

In FIG. 3F, balloon 77 is deflated after disruption of lesion S. Emboli E generated during the procedure are directed into removal port 76 via the established retrograde flow. The emboli travel downstream within lumen 75 and may be removed via filter 30. Filtered blood then may be returned to the body via venous return line 32.

Upon completion of the medical procedure, instrument 78 is retracted into catheter 74. Occlusive member 73 then is deflated via inflation port 24, which in turn causes antegrade flow to become re-established in treatment vessel T. The apparatus then may be removed from the patient's vessel.

Figure 4A:
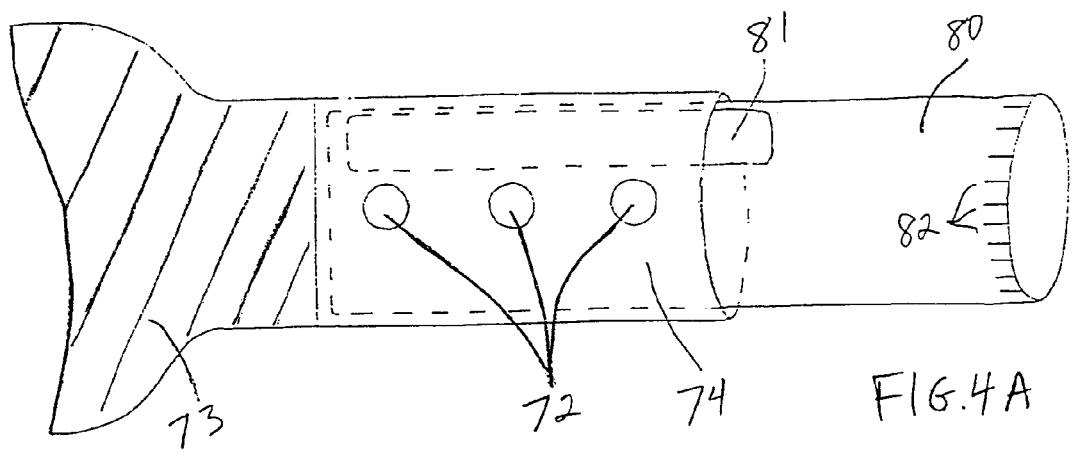
FIGS. 4A–4B are detailed views of the distal end of the catheter of the present invention showing an illustrative inner sheath suitable for adjusting the flow through the blood intake port.
Figure 4B:
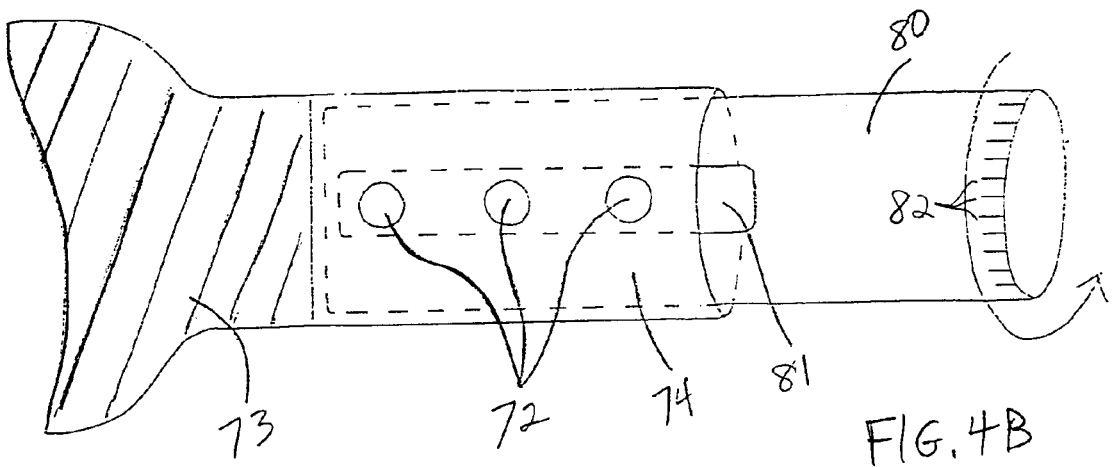

Referring to FIGS. 4A–4B, apparatus and methods for controlling retrograde flow through the catheter of the present invention are provided. Catheter 74 comprises inner sheath 80 having opening 81. In a preferred embodiment, opening 81 is a slot having a rectangular area greater than the cumulative area of blood intake ports 72. In an alternative embodiment, opening 81 may instead comprise a plurality of openings that correspond to each one of blood intake ports 72.

In FIG. 4A, opening 81 is positioned such that it does not overlap with intake port 72. In this closed scenario, a solid region of inner sheath 80 covers blood intake port 72 to prohibit external fluid from entering catheter 74. When inner sheath 80 is rotated relative to its longitudinal axis, as shown in FIG. 4B, opening 81 coincides with intake port 72 such that fluid may enter catheter 74 and flow in a retrograde direction, i.e., away from occlusive member 73. The proximal end of inner sheath 80 may comprise markings 82 that enable the operator to know the exact position of opening 81 with respect to intake port 72. This is useful for determining the corresponding area that is exposed to flow, and provides a reliable mechanism for fully or partially exposing blood intake ports 72.

In an alternative embodiment, inner sheath 80 may slide longitudinally within catheter 74 such that opening 81 covers and uncovers intake port 72 via a longitudinal sliding motion. Alternatively, opening 81 may be omitted and the distalmost end of inner sheath 80 may cover and uncover intake port 72 using a longitudinal sliding motion.

Figure 5A:
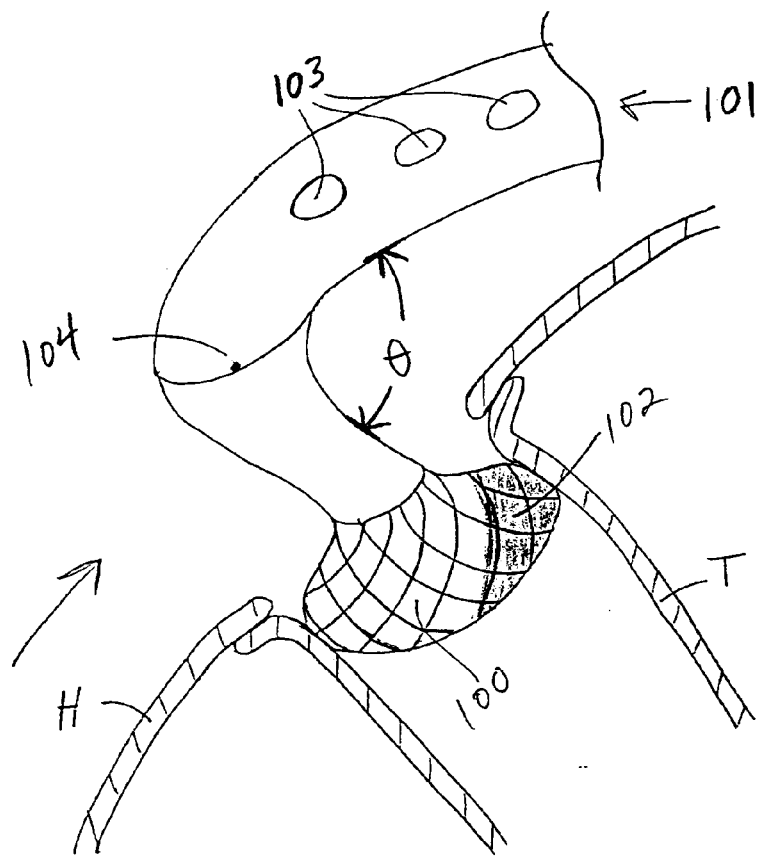

Referring now to FIG. 5A, an alternative embodiment for the occlusive member is described. Catheter 101 comprises mechanical occlusive member 100 having a wire weave configuration, preferably constructed of a shape-memory retaining material, for example, a Nickel Titanium alloy (commonly known in the art as Nitinol).

The use of Nitinol generally requires the setting of a custom shape by manufacturing methods which are per se known, such as setting the pre-determined shape by constraining the Nitinol element on a mandrel or fixture of the desired shape, then applying an appropriate heat treatment.

Mechanical occlusive member 100 advantageously provides an occlusive member having a maximum removal diameter, i.e., approximately the inner diameter of treatment vessel T. Mechanical occlusive member 100 lies flush with the intimal layer of treatment vessel T to facilitate removal of relatively large emboli into the lumen of catheter 101. Mechanical occlusive member 100 may be deployed, for example, by proximally retracting an outer sheath that initially compresses the occlusive member within the sheath.

Mechanical occlusive member 100 preferably is covered by elastomeric polymer 102, such as latex, polyurethane or polyisoprene. Elastomeric polymer 102 preferably is a composition wherein the chemical bonds have less cross linking to allow for greater elastic properties.

A bent region, knee 104, is formed proximal to occlusive member 100 and distal to blood intake port 103, as shown in FIG. 5A. Knee 104 comprises an angle θ that may be fixed or flexible. Several knee variations are described hereinbelow.

Figure 5B:
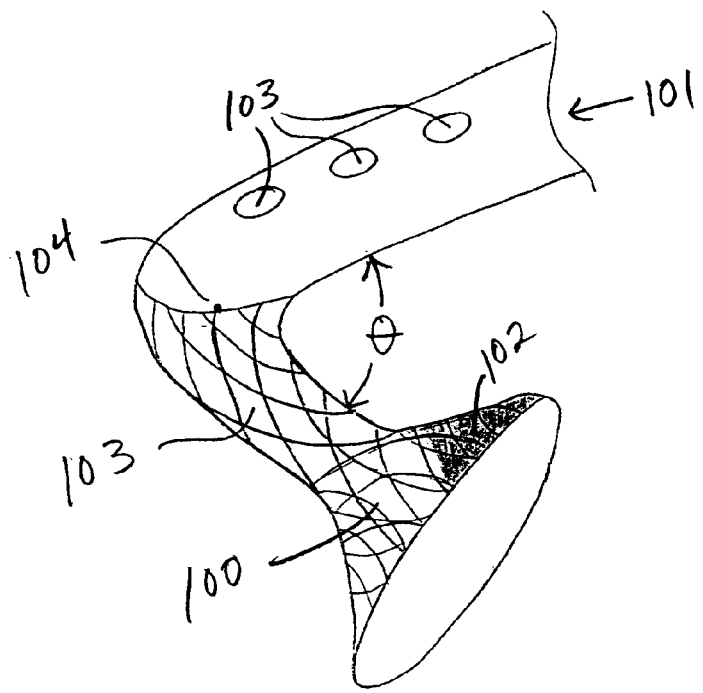

Alternatively, mechanical occlusive member 100 may span a greater distance, as shown in FIG. 5B. The wire weave configuration at the distal end comprises mechanical occlusive member 100 and midsection 103, a section connecting mechanical occlusive member 100 with knee 104. Midsection 103, provided in a wire weave configuration and covered by elastomeric polymer 102, may provide more flexibility and less kinking than a solid midsection.

Referring to FIG. 6A, mechanical occlusive member 118 comprising a plurality of split ends 120 is shown in a contracted states, such as when disposed within an outer sheath (not shown). When the sheath is retracted proximally, the split ends self-expand to the configuration shown in FIG. 6B. Split ends 120 are preferably made from a shape memory material such as Nitinol, and are heat treated to form a predetermined shape. Elastomeric polymer 122 is adhered to the outer surface of split ends 120 to form a blood impermeable membrane suitable for occluding flow and removing emboli.

Referring to FIG. 7A, mechanical occlusive member 126 is provided in a self-expanding woven wire mesh. Occlusive member 126 is inserted transluminally in a retracted state, for example, by compressing woven mesh 130 within outer sheath 128. As outer sheath 128 is retracted proximally, mesh 130 returns to a predetermined, deployed configuration having removal port 132, as shown in FIG. 7B. Removal port 132 is substantially flush with the intimal layer of the treatment vessel. Woven mesh 130 preferably is coated with an elastomeric polymer to form a blood impermeable membrane.

Referring to FIG. 8A, self-expanding mechanical occlusive member 136 having woven wire mesh 140 is provided in a retracted state within outer sheath 138. As outer sheath 138 is retracted proximally, the mesh self-expands to the rounded shape shown in perspective in in FIG. 8B and from a side sectional view in FIG. 8C. Mechanical occlusive member 136 comprises removal port 144, internal lip 150, midsection 142, and an elastomeric polymer coating covering the wire weave along its length. As embolic particles enter removal port 144 via venturi-assisted flow, they may either become trapped within internal lip 150 or funneled into midsection 142 for subsequent removal.

Figure 9A:
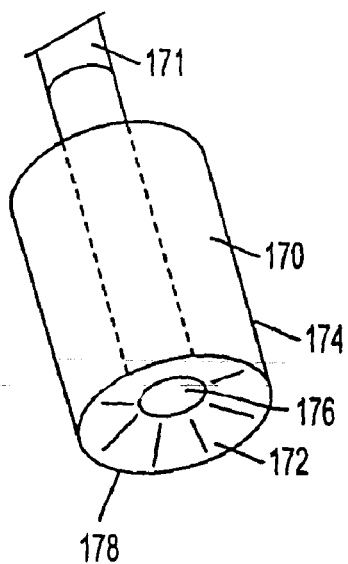
Figure 9B:
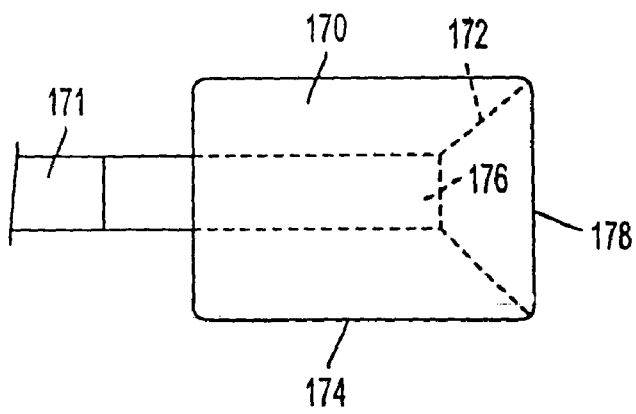

Referring to FIGS. 9A and 9B, inflatable occlusive member 170 is described. Compliant occlusive member 170 may be inflated via inflation port 24 of FIG. 1. Outer surface 174 of occlusive member 170 is configured to engage the treatment vessel wall over a relatively large area. Distal taper 172 facilitates embolic removal by providing a distal-most edge 178 having a diameter substantially equal to the inner diameter of the vessel. Distal taper 172 provides a smooth particle transition from distal-most edge 178 into lumen 176 of catheter 171.

Figure 10A:
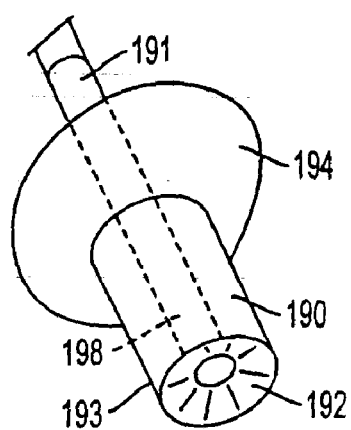
Figure 10B:
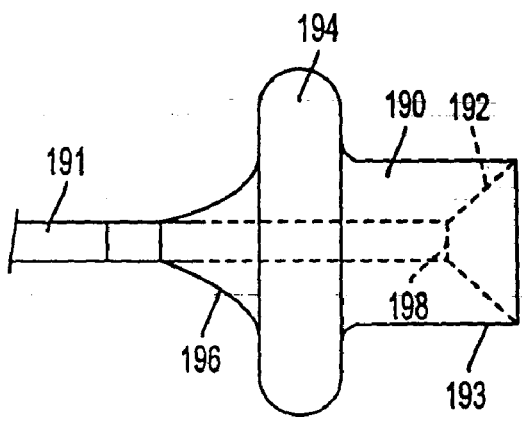
Figure 11A:
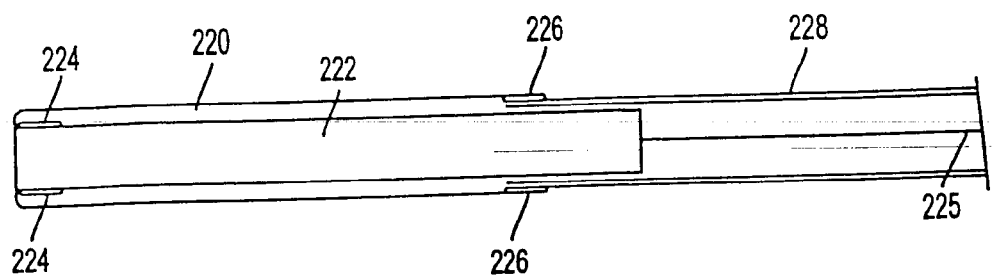
Figure 11B:
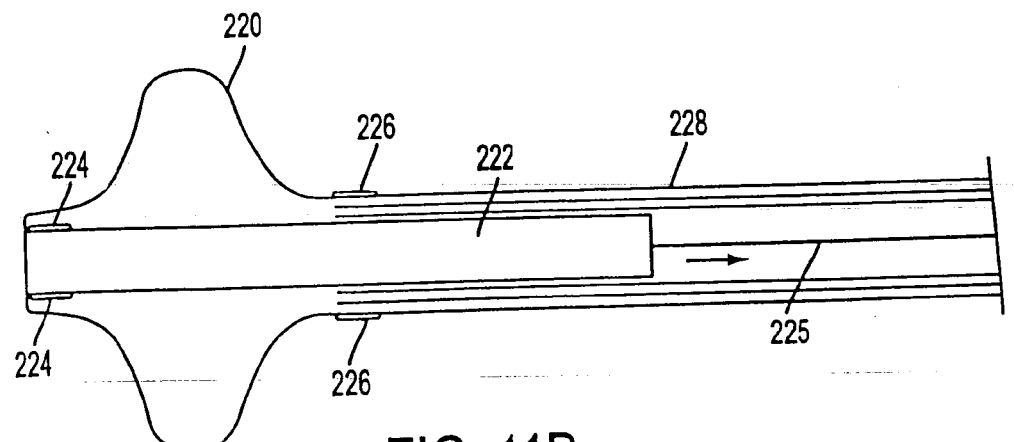
Figure 12:
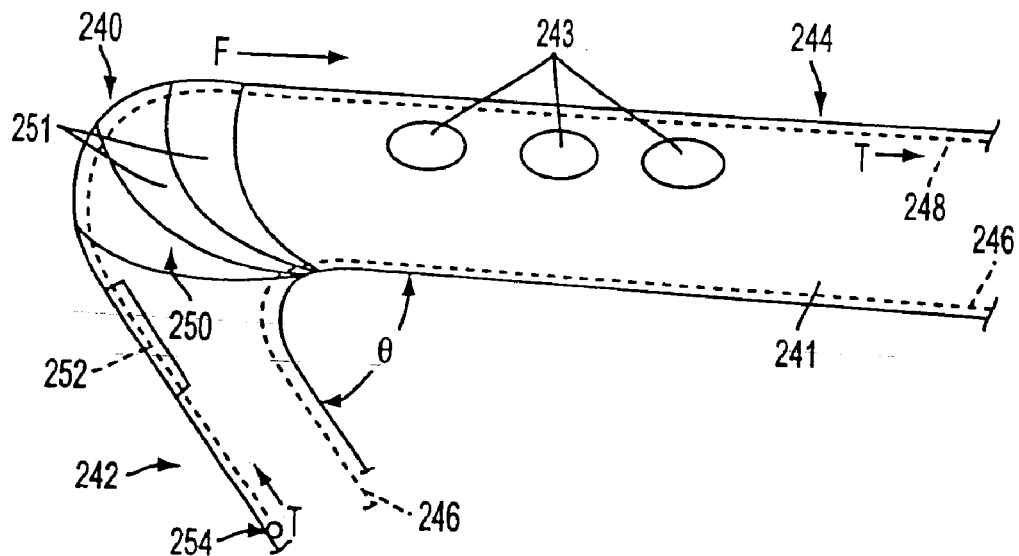
Figure 13:
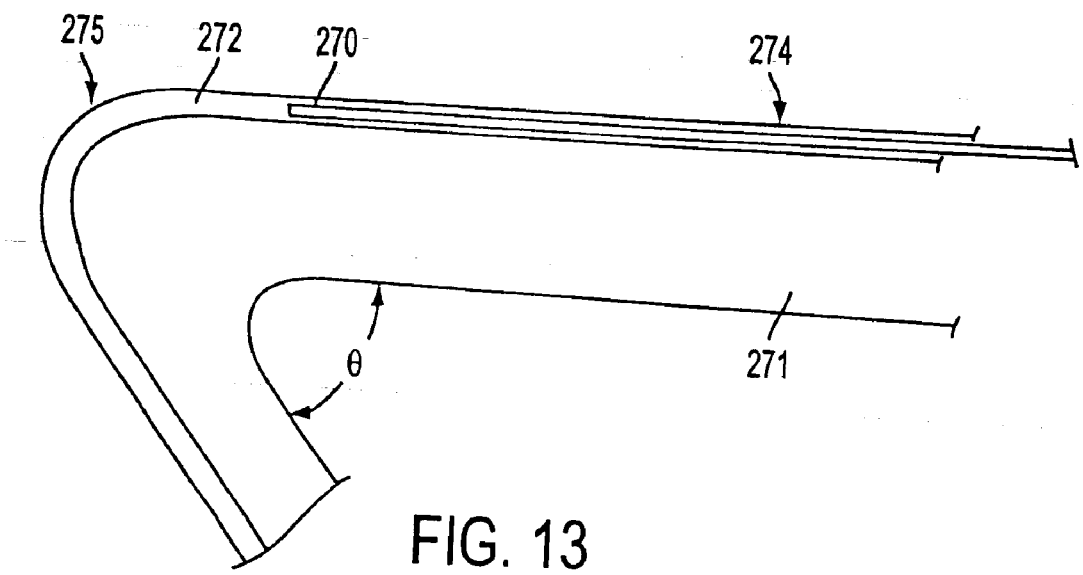
Figure 14:
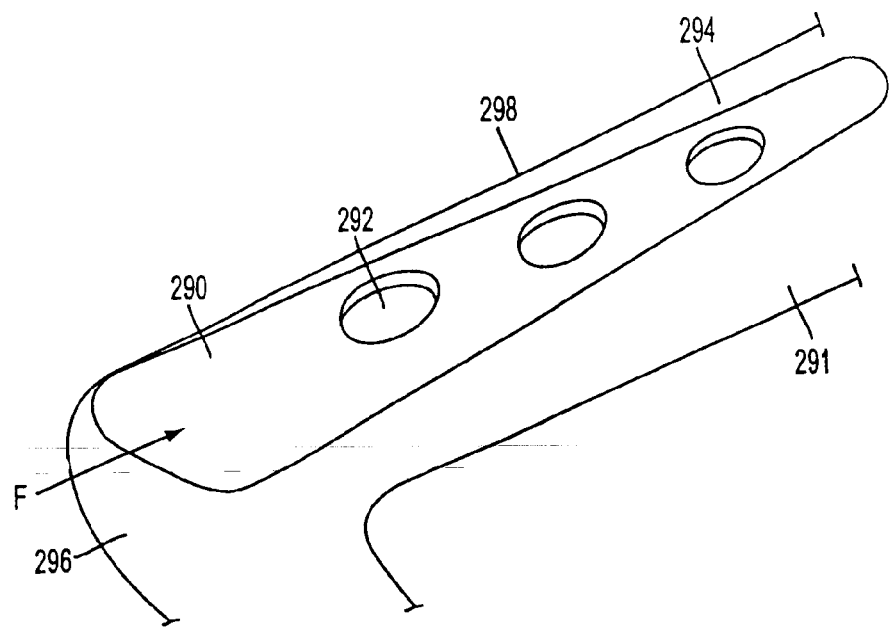
Figure 15:
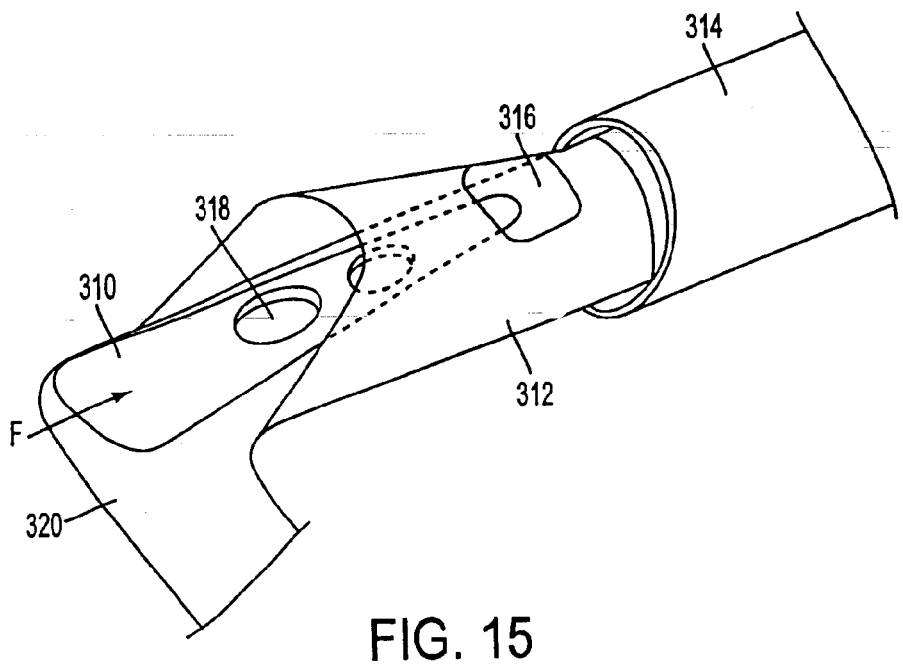
Figure 16A:
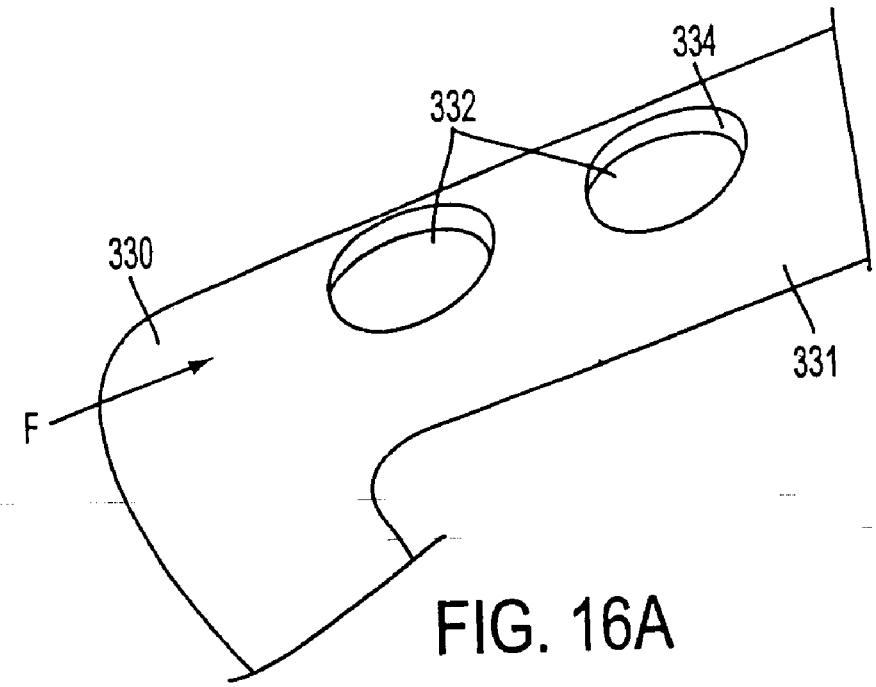
Figure 16B:
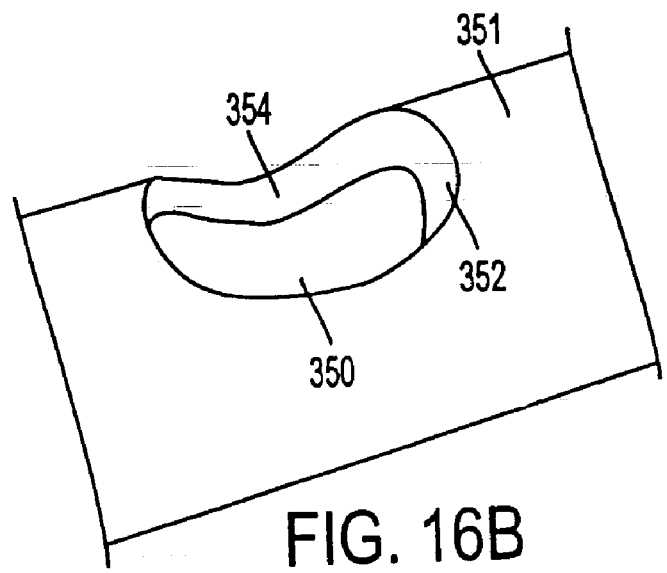

Referring to FIGS. 10A and 10B, a further alternative embodiment of inflatable occlusive member 190 is described. Outer surface 193 of occlusive member 190 engages the treatment vessel wall over a relatively large area, while cuff 194 provides an atraumatic seal around the ostium of the treatment vessel. Cuff 194 allows the main body of catheter 191 to move without injuring or breaking the seal of the treatment vessel. Inflatable support region 196 provides structural stability for cuff 194. Distal taper 192 facilitates a smooth transition into lumen 198 of catheter 191.

FIG. 11 illustrate another alternative occlusive member having flexible sheath 220. Flexible sheath 220 comprises a compliant material, e.g., polyurethane, latex or polyisoprene. Flexible sheath 220 is affixed to piston 222 at a distal location by adhesives 224, and affixed to catheter body 228 at a proximal location by adhesives 226. Piston 222 is initially disposed at a distal-most location, such that flexible sheath 220 is stretched and substantially parallel to catheter 228, as shown in FIG. 11A. Upon actuation, piston 222 retracts proximally within catheter 228, such that the distal end of flexible sheath 220 is retracted with respect to its proximal end. This compresses the air within the sheath and causes the sheath to bulge outward, as shown in FIG. 11B. The bulge provided by flexible sheath 220 may be configured to atraumatically seal the ostium of the treatment vessel.

Figure 11A:
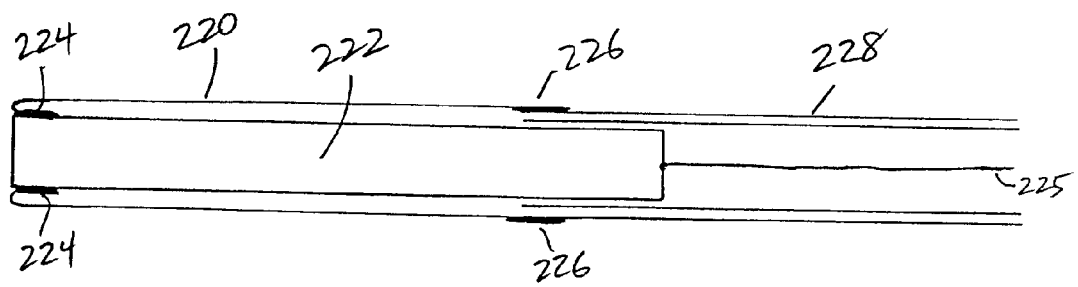
Figure 11B:
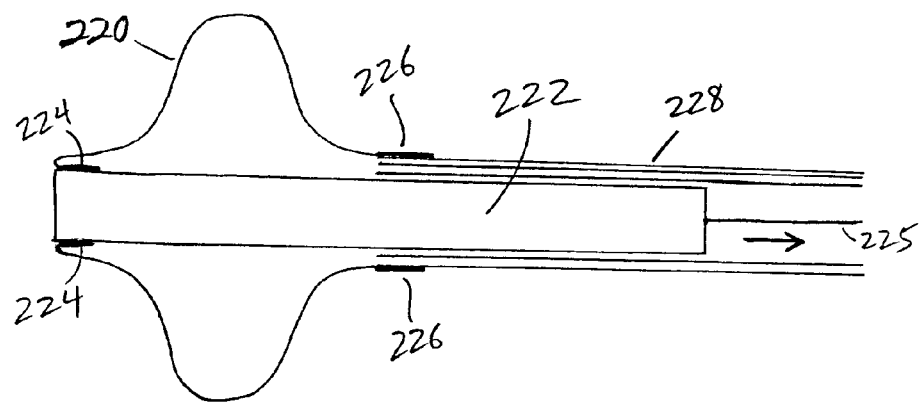

Actuation of piston 222 may occur, for example, by providing cable 225 affixed to the proximal end of piston 222. Upon proximal retraction of cable 225, piston 222 is retracted proximally to form the bulge of sheath 220, as shown in FIG. 11B. Upon completion of the procedure, cable 225 or an alternative straightening means may be advanced distally, to advance piston 222 to a distal-most position and collapse sheath 220.

Alternatively, piston 222 may be actuated by applying a suction force suitable for retracting piston 222 within the catheter. The suction may be provided, for example, from a syringe attached to a proximal hub assembly and through a lumen that communicates with piston 222. Upon completion of the procedure, pressure may be applied within the lumen to return piston 222 to a distalmost position and collapse sheath 220.

Figure 12:
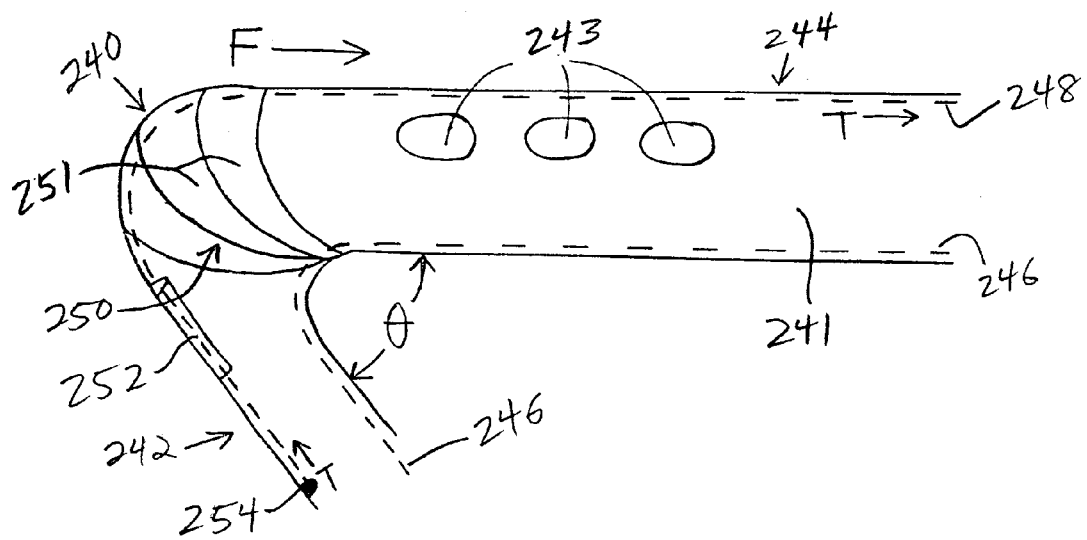
FIGS. 12–13 illustrate mechanisms for bending the catheter in the vicinity of the distal end to engage the ostium of a treatment vessel.

Referring to FIG. 12, features of the knee portion of catheter 241 are described. Knee 240 is located proximal to the occlusive member and distal to blood intake port 243. Knee 240 provides a bend, defined by angle θ, that allows distal access to the treatment vessel while allowing the proximal end of catheter 241 to reside within the host vessel. Knee 240 may be configured in a fixed or variable angle assembly. Distal region 242 may be anchored within the ostium of the treatment vessel, and angle θ may be varied to manipulate flow characteristics of the system. For example, increasing angle θ may cause proximal region 244 to become biased into the direction of blood flow F such that more blood flows into blood intake port 243. The increased flow into catheter 241 may vary the level of aspiration at the treatment site due to a varied venturi effect.

FIG. 12 illustrates a means for varying angle θ comprising shape memory member 246, tensioning member 248, and optional flexing member 250. Flexing member 250 contains a plurality of bellow-type sections 251 that may either expand or overlap to increase or decrease angle θ, respectively.

During transluminal insertion of the device, shape memory member 246 is provided in a retracted state, for example, by compressing the member within an outer sheath, such that distal section 242 and proximal section 244 are substantially parallel. Upon deployment, e.g., proximally retracting the outer sheath, shape memory member 246 returns to its predetermined configuration, having a substantially acute angle θ. Shape memory member 246 may be set to return to its expanded configuration by heat treating a piece of Nitinol according to methods described hereinabove.

Tensioning member 248 opposes shape memory member 246 within catheter 241. Tensioning member 248 spans the length of catheter 241 and is affixed at distal point 254 by an adhesive. An additional lumen 252 may be used to guide tensioning member 248 within the catheter. Since the initial deployment of shape memory member 246 provides a substantially acute angle θ, tension may be applied to tensioning member 248 to pull distal point 254 such that knee 240 bends and angle θ increases.

Figure 13:
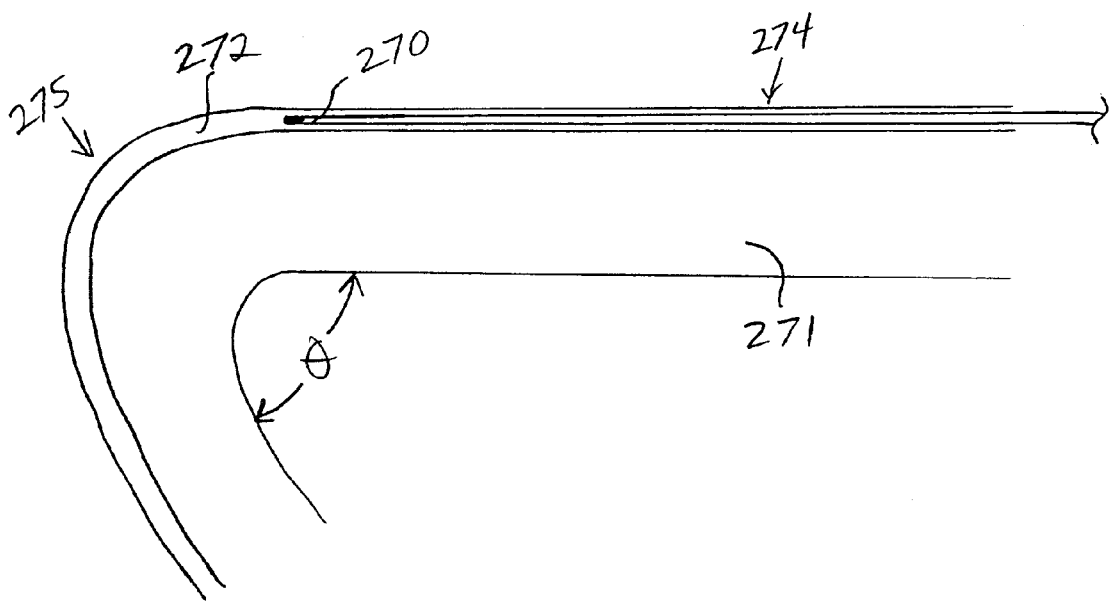

Referring to FIG. 13, an alternative means for varying angle θ of knee 275 is described. In this embodiment, the device comprises straightening wire 270 and lumen 272. Lumen 272 is sized to permit longitudinal sliding of wire 270 within catheter 271. Straightening wire 270 is initially positioned within proximal region 274 of catheter 271, and knee 275 is provided in a configuration having a substantially acute angle θ. Straightening wire 270 then may be advanced distally to push against the inner wall of knee 275 to increase angle θ. Additionally, straightening wire 270 may be retracted proximally to alleviate the pressure against knee 275 to decrease angle θ.

Figure 14:
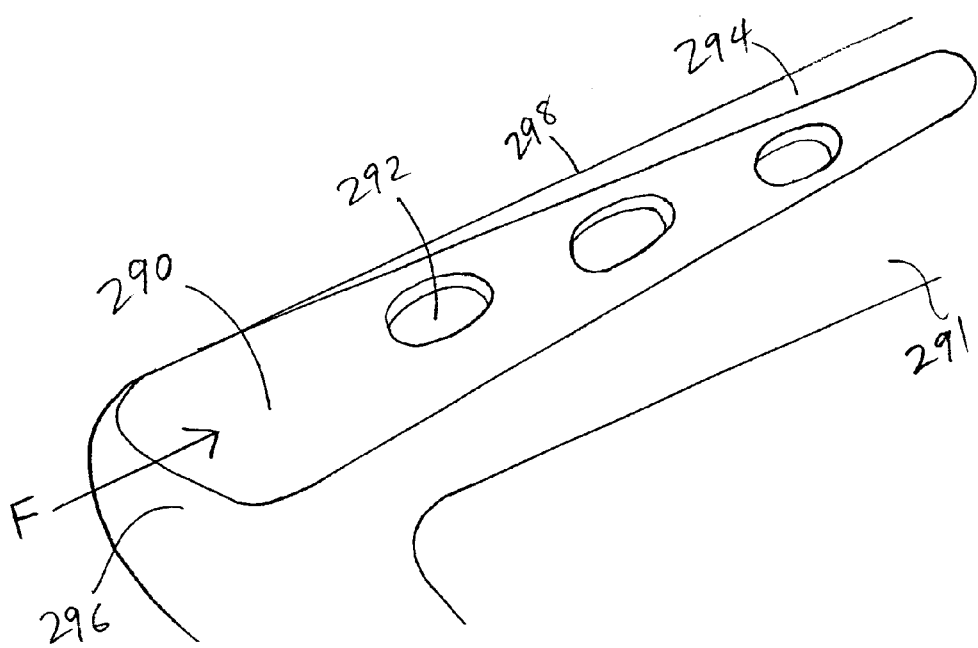
FIG. 14 shows a further alternative embodiment of a catheter constructed in accordance with the present invention having a plurality of blood intake ports disposed on a flat plane.

Referring to FIG. 14, means for improving flow interaction between the host vessel and blood intake ports 292 are provided. In this embodiment, flat plane 290 houses blood intake port 292. Taper 298 spans from knee 296 to a location proximal to blood intake port 292. Blood flow F occurs in the direction indicated along flat plane 290, and side walls 294 formed by taper 298 help channel blood into blood intake port 292.

Figure 15:
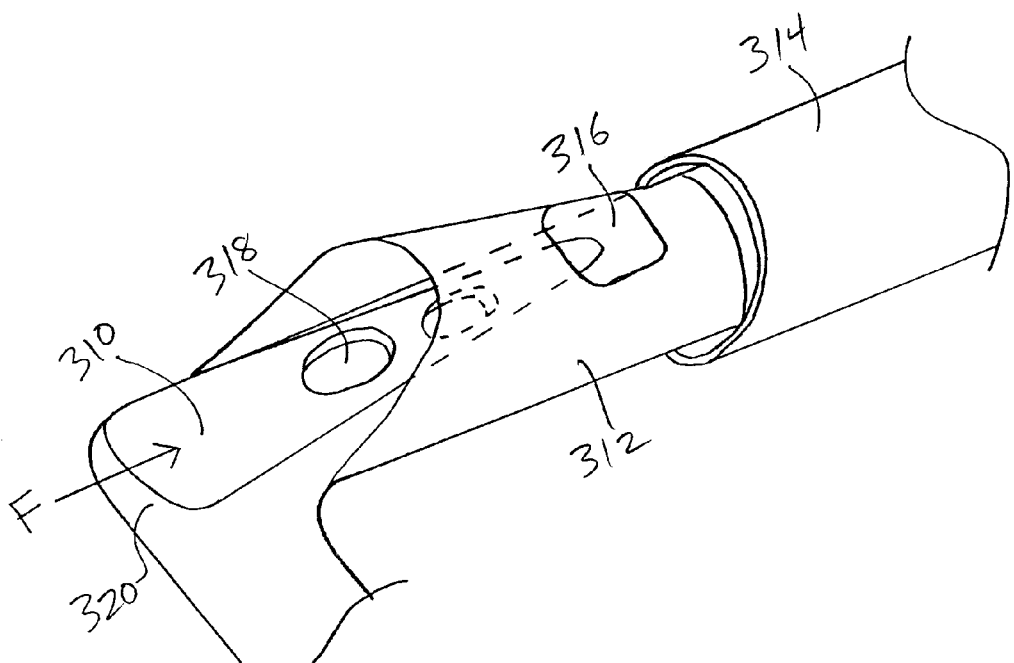
FIG. 15 depicts a catheter including a hood suitable for directing blood into the blood intake ports.

As illustrated in FIG. 15, a hood also may be used to more efficiently direct blood into the intake ports. Self-expanding hood 312 that may be manufactured, for example, from shape memory materials according to methods described hereinabove. Hood 312 is initially provided in a collapsed state within slidable outer sheath 314. As outer sheath 314 is retracted proximally, hood 312 deploys to a predetermined, expanded shape. As outer sheath 314 is advanced distally, hood 312 again is collapsed within the sheath.

As blood flow F occurs in the host vessel, hood 312 may direct flow more efficiently into blood intake port 318. Blood vent 316 may be provided to allow flow F that is not directed into blood intake port 318 to exit hood 312 and continue flowing within the host vessel. Outer sheath 314 may be advanced distally to cover blood vent 316, without collapsing hood 312, to increase the flow of blood into intake port 318.

Figure 16A:
FIGS. 16–19 are views of alternative blood intake port configurations.
Figure 16B:
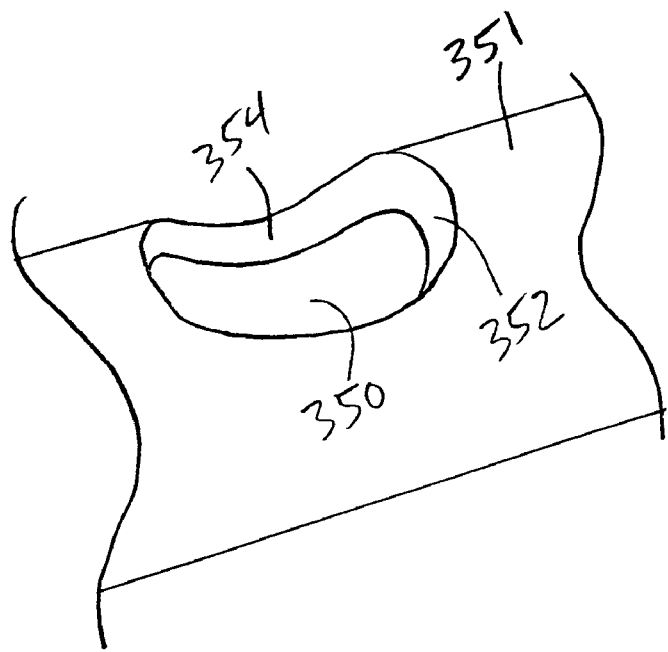

Referring now to FIG. 16A, the catheter body is substantially round along its length. The diameter of blood intake port 332 may be varied to increase or decrease the amount of blood flow into the lumen of catheter 331. Additionally, proximal edges 334 of blood intake port 332 may be varied, i.e., flat or angled, to better direct blood flow F into the lumen of catheter 331. FIG. 16B illustrates an alternative configuration of blood intake port 350 wherein proximal edge 352 and side edge 354 are angled to provide better blood channeling ability. A hood similar to hood 312 of FIG. 15 may be used with the round catheter body depicted in FIG. 16.

Figure 17:
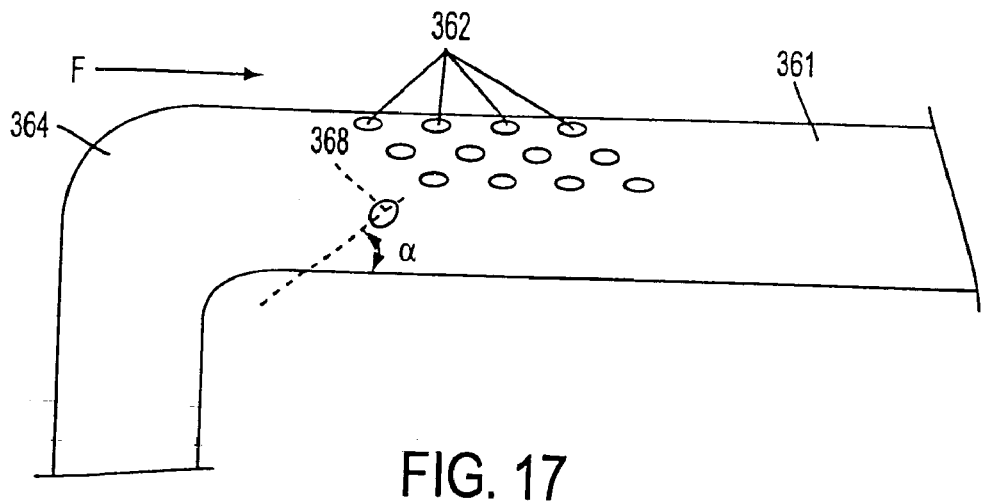

Referring to FIG. 17, catheter 361 comprises a plurality of shaped holes having defined blood intake patterns 362. Patterns 362 may be provided on one side of the catheter or both sides to improve blood flow F into catheter 361. Additionally, the blood intake ports may be cut at an angle α with respect to the catheter body to enhance flow channeling ability. For example, while blood intake patterns 362 are illustrated as being parallel to blood flow F, blood intake port 368 is provided at an angle α with respect to blood flow F to better direct flow into intake port 368.

Figure 18A:
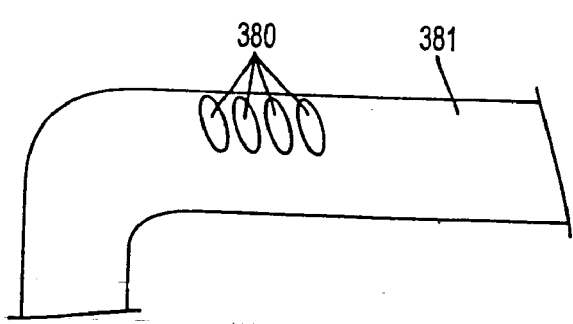
Figure 18B:
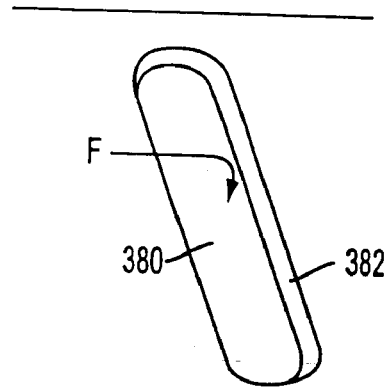

In an alternative embodiment, the blood intake port may be provided in a slot or groove configuration, as shown in FIG. 18A. Slots 380 are provided either singularly or in combination. Proximal wall 382 of slot 380 may be angled to increase the blood flow F into slot 380, as shown in FIG. 18B.

Figure 19:
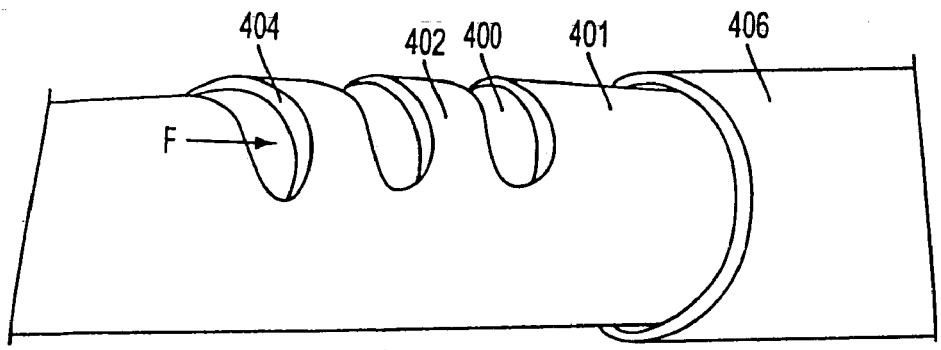
Figure 20:
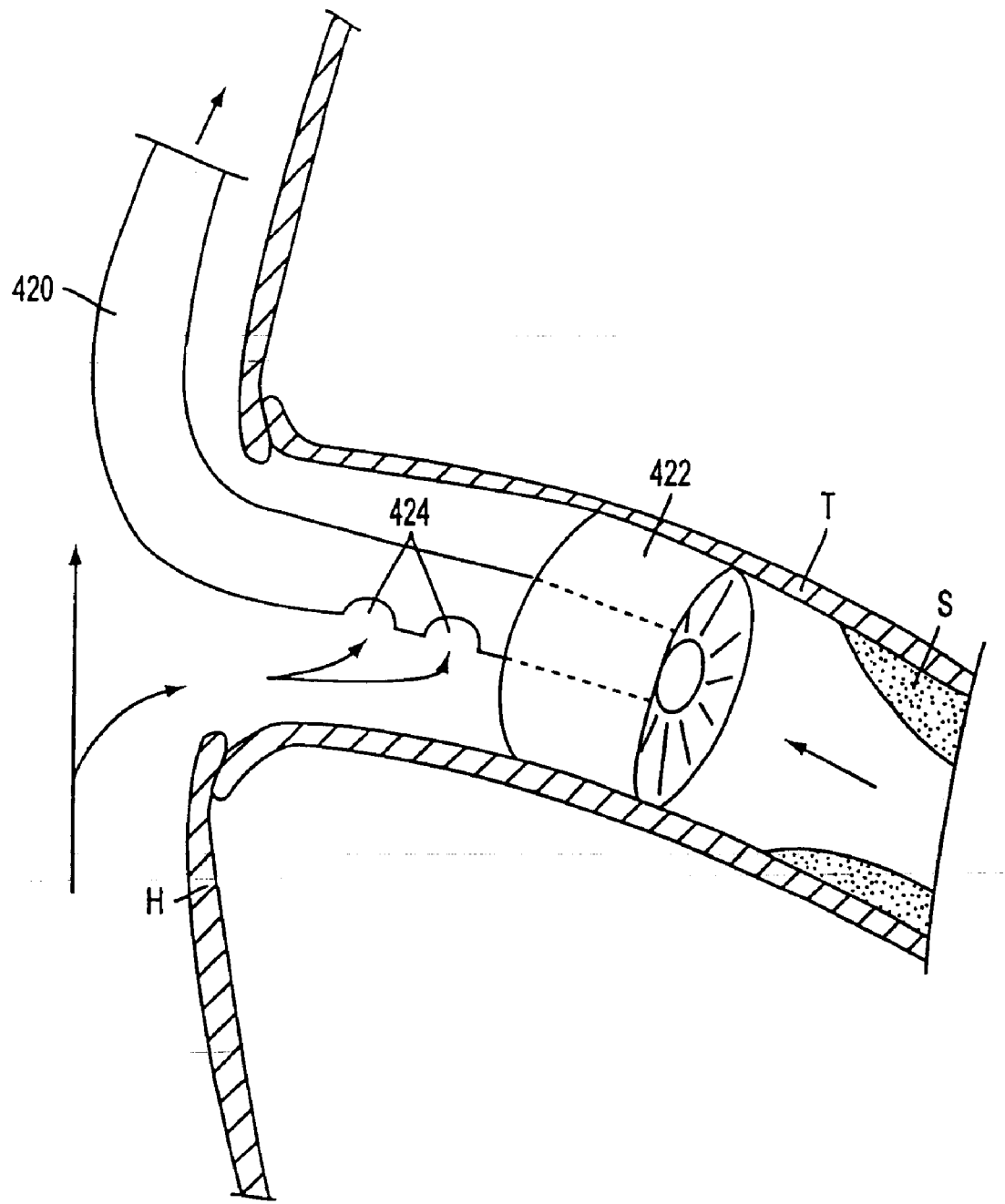
Figure 21:
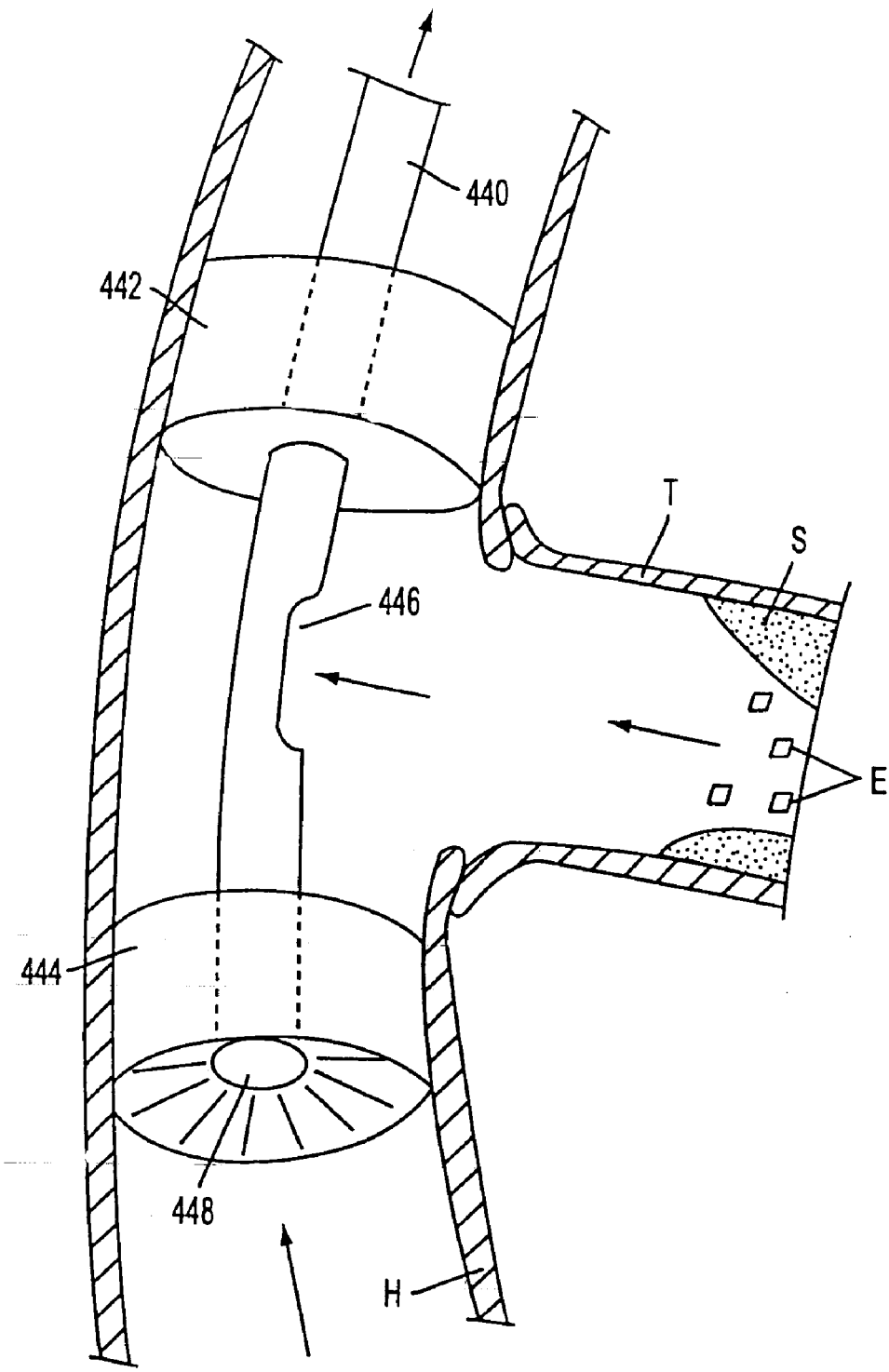

Finally, the slots themselves may be outwardly biased, for example, by heat setting the shape of the catheter body to form deployable sections 402, as shown in FIG. 19. In this embodiment, proximal edge 404 of blood intake port 400 is raised with respect to catheter 401 to better direct flow F into intake port 400. Deployable sections 402 may be compressed within outer sheath 406 in a retracted state for transluminal insertion of the device. Outer sheath 406 then is retracted proximally to return deployable sections 402 to their pre-determined, expanded state having raised proximal edges 404. Upon completion of the procedure, outer sheath 406 is advanced distally to collapse the raised edges within the sheath.

Figure 20:
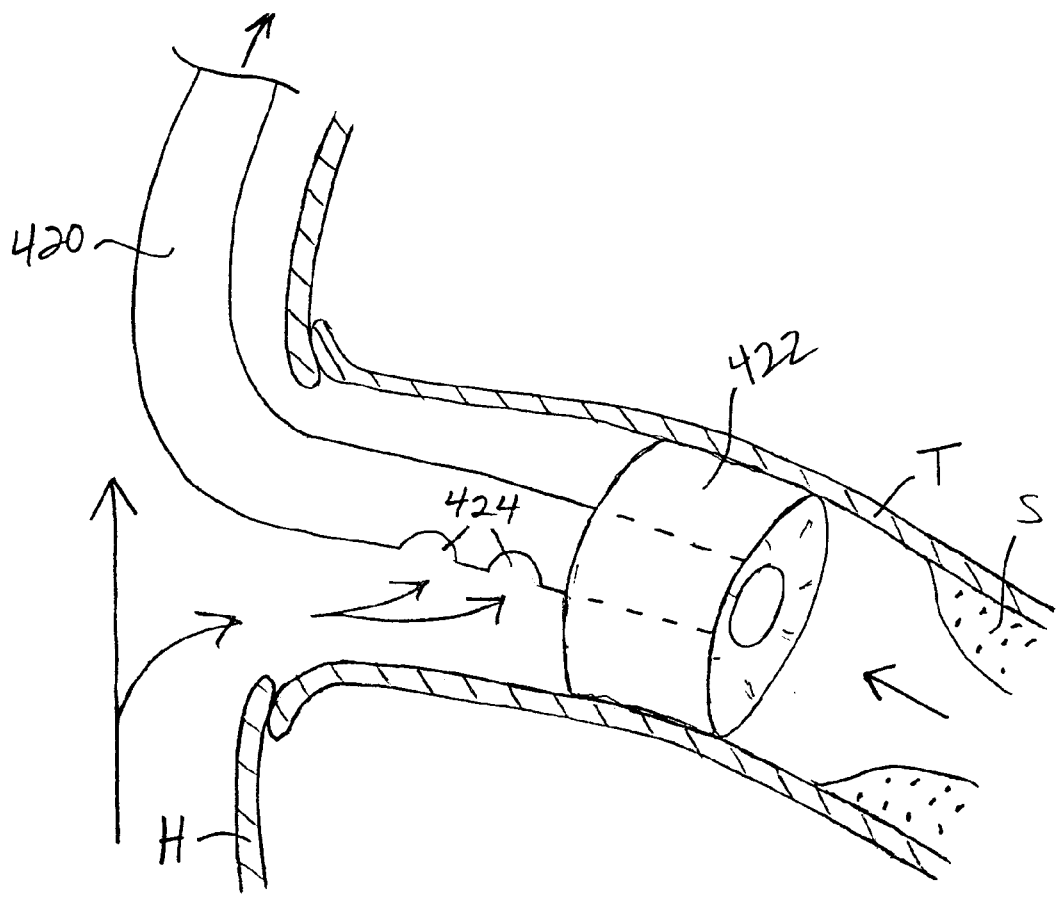
FIG. 20 illustrates a catheter having at least one intake port positioned within the treatment vessel.

Referring to FIG. 20, blood intake port 424 of catheter 420 is positioned within treatment vessel T having lesion S. In this embodiment, occlusive member 422 is positioned within treatment vessel T, as opposed to being positioned within the ostium. This allows blood intake port 424 to be positioned within treatment vessel T such that antegrade flow from host vessel H may enter treatment vessel T and may flow into blood intake port 424, to cause a venturi effect in treatment vessel T.

Figure 21:
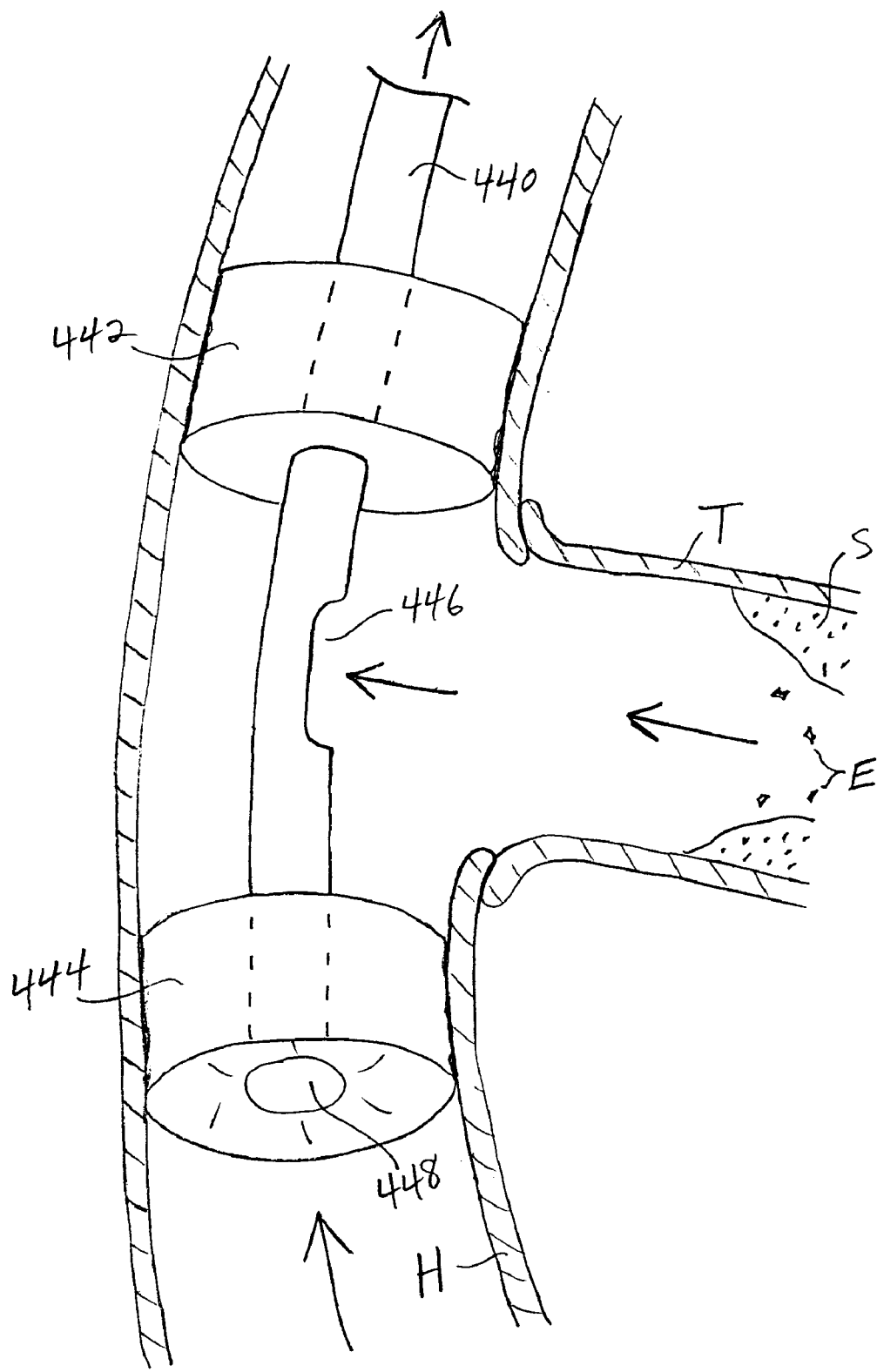
FIG. 21 shows a further alternative embodiment of a catheter constructed in accordance with the present invention having two occluding members and at least one intake port that communicates with flow from the treatment vessel.
Figure 1:
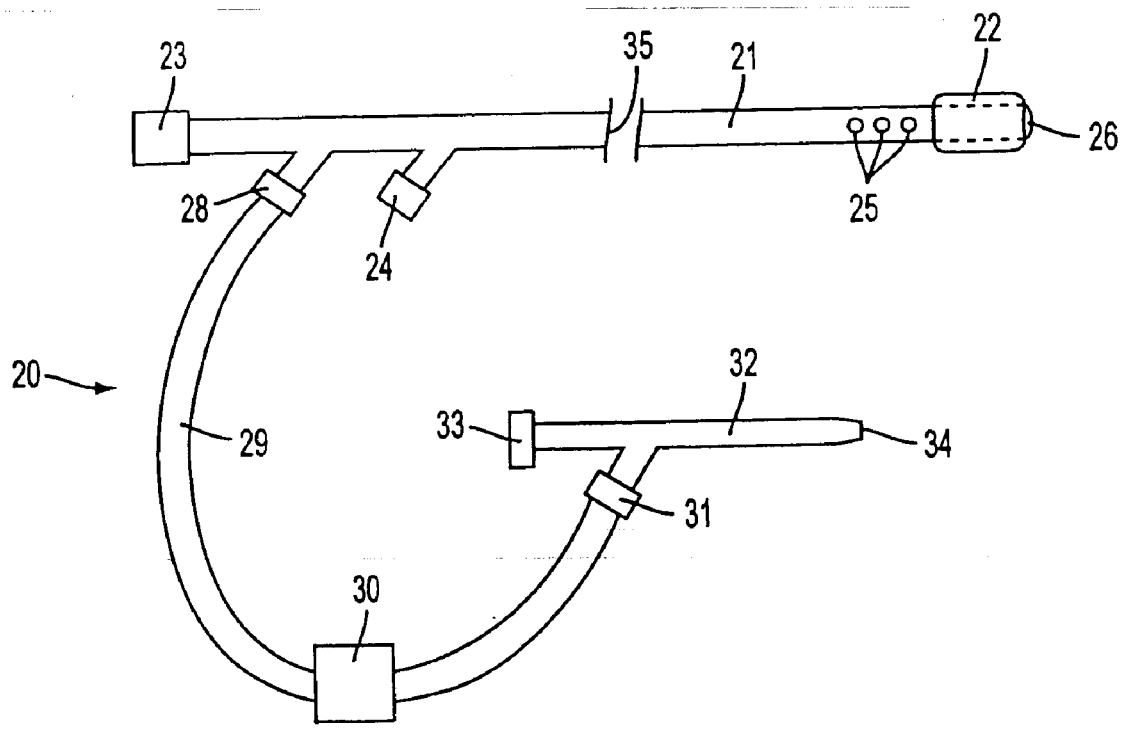
Figure 2:
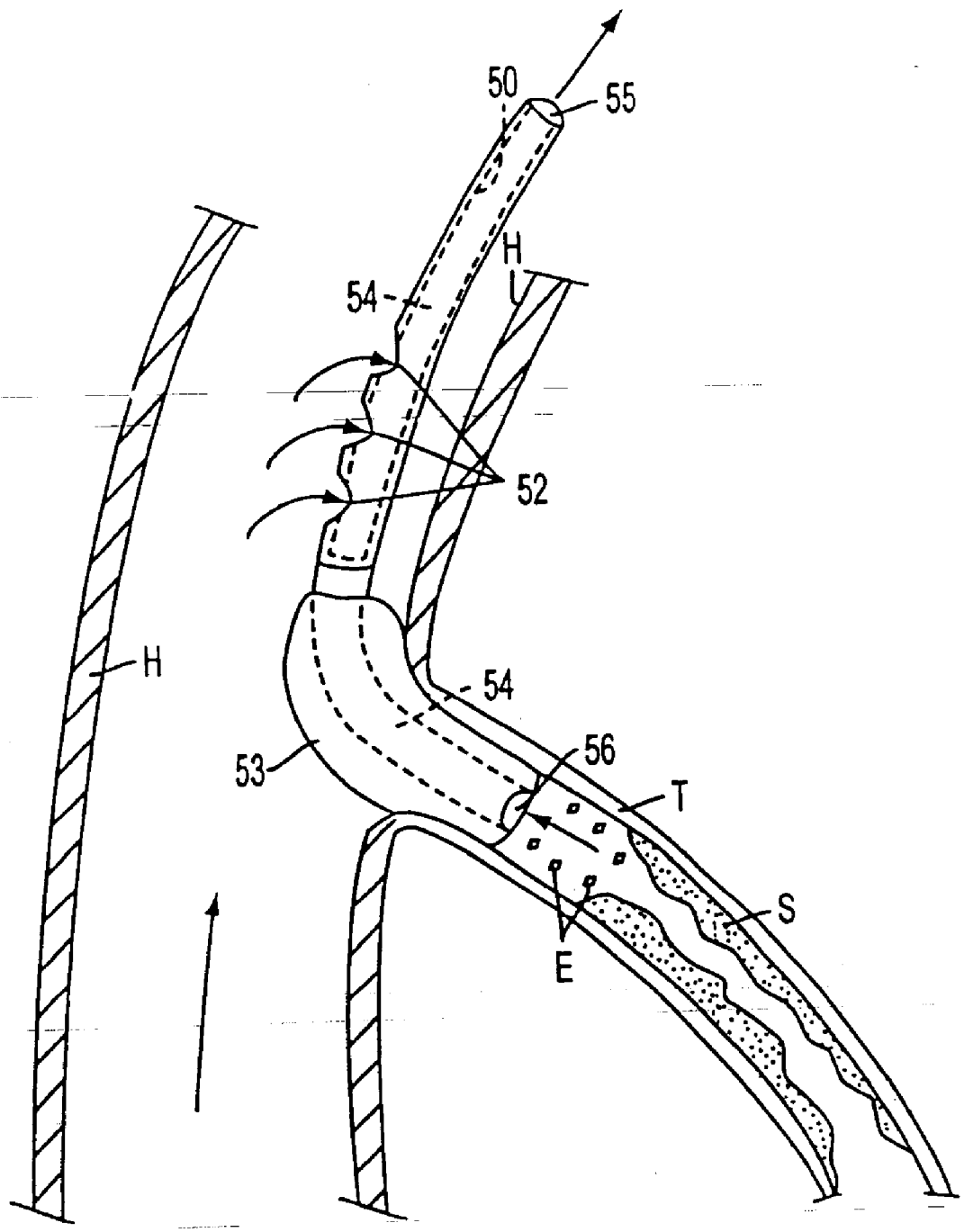
Figure 3B:
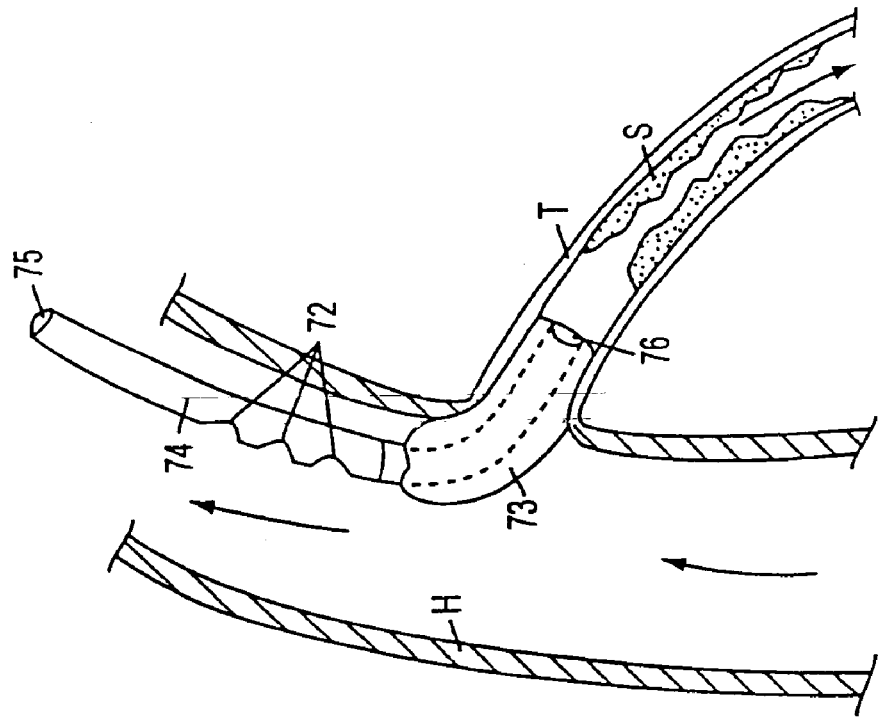
Figure 3A:
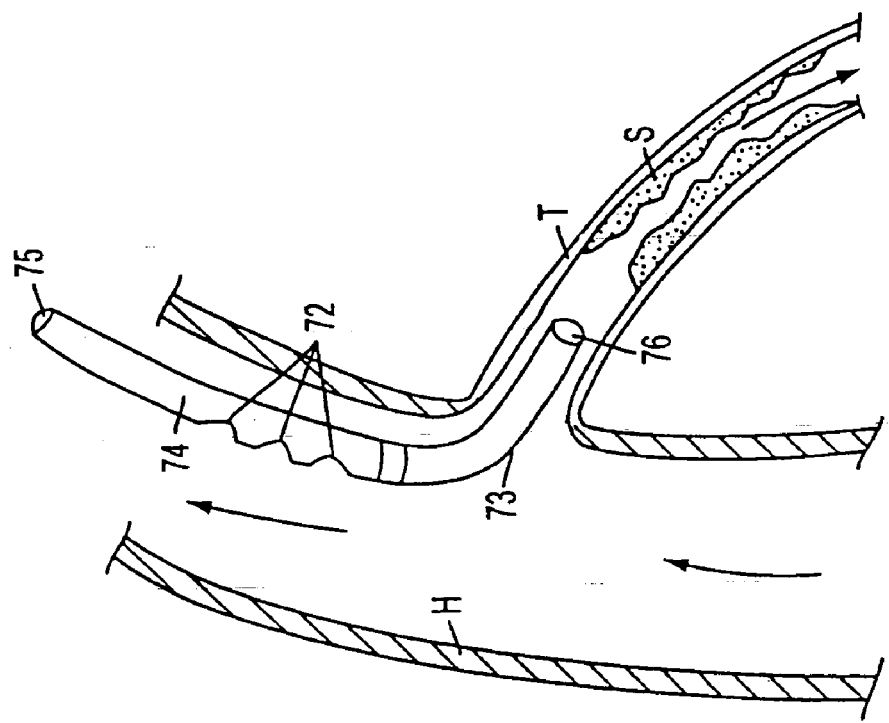
Figure 3D:
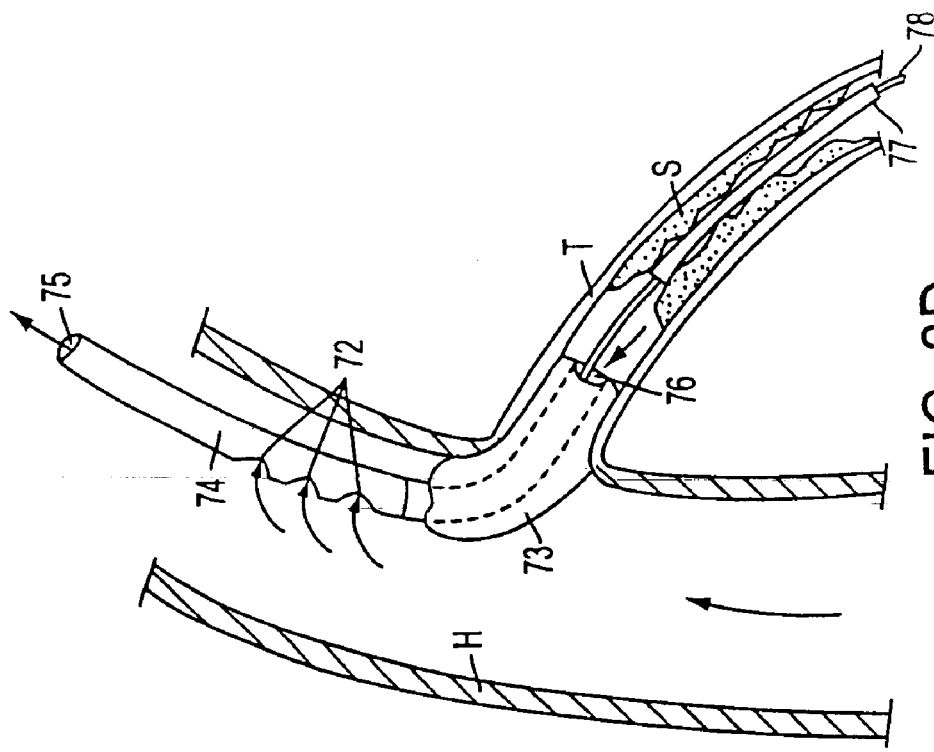
Figure 3C:
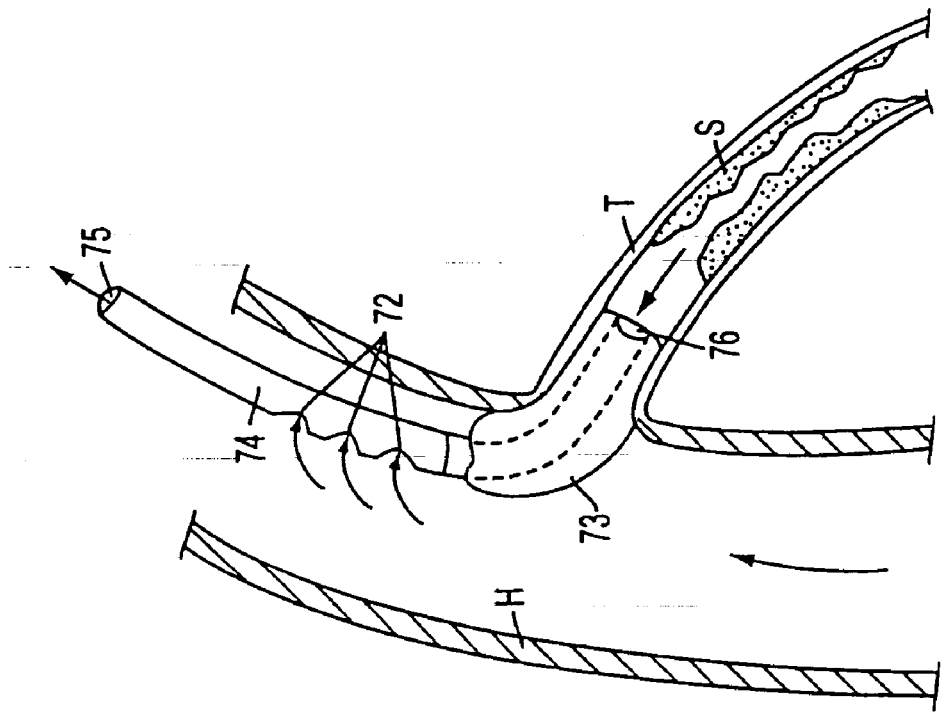
Figure 3F:
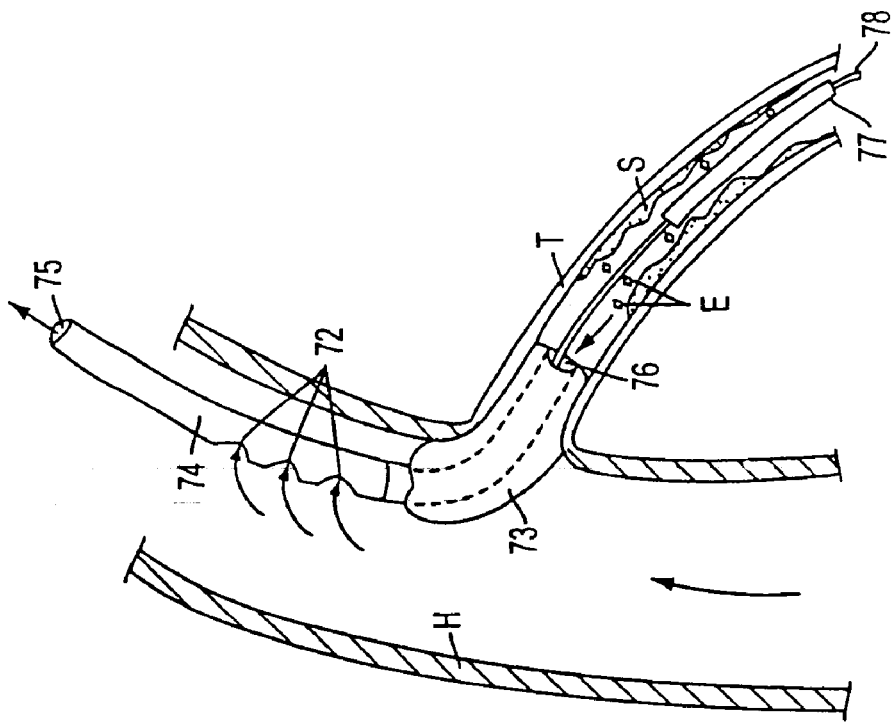
Figure 3E:
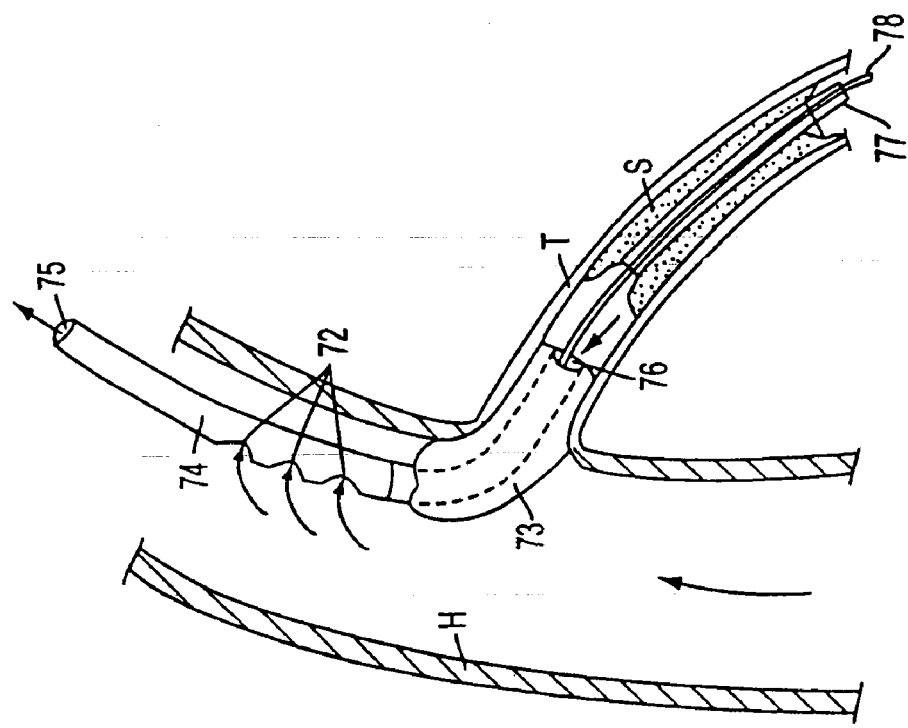
Figure 4A:
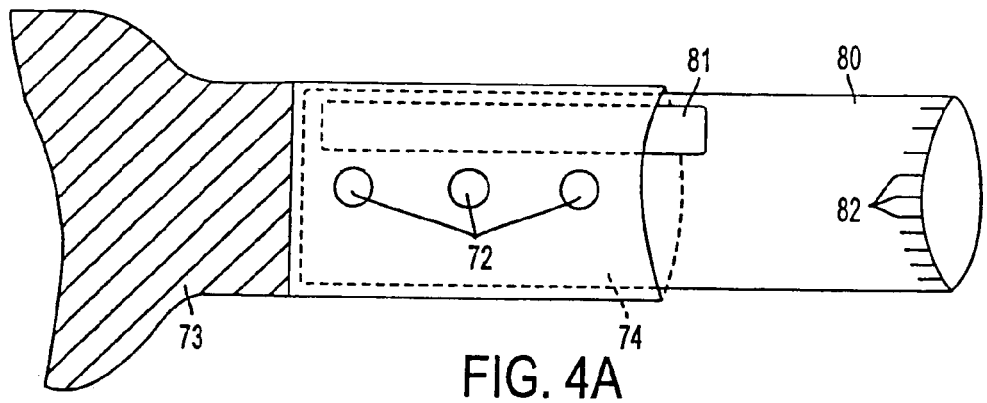
Figure 4B:
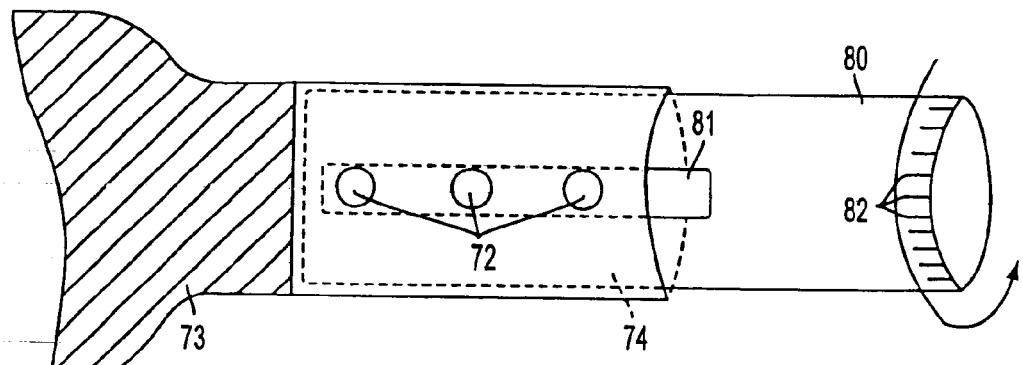
Figure 5A:
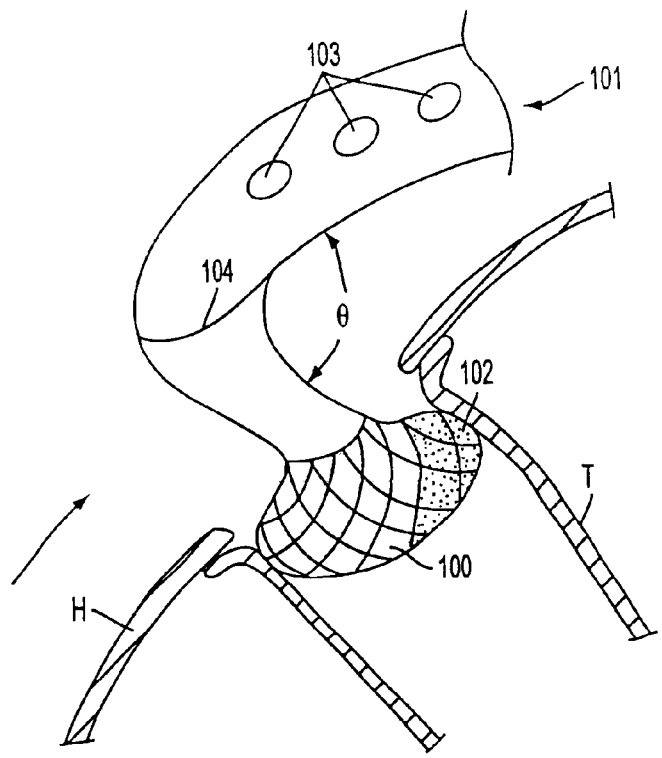
Figure 5B:
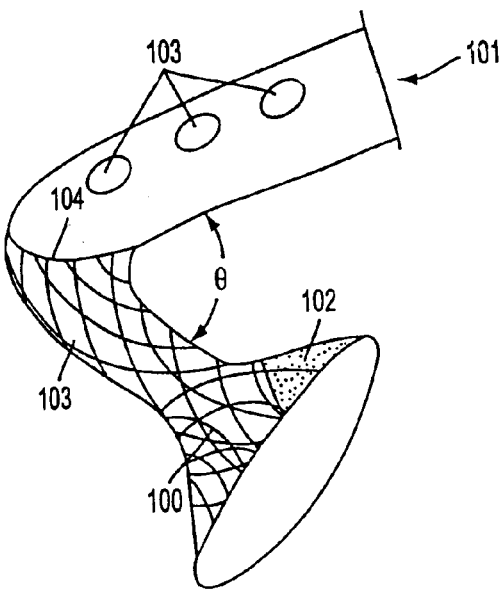

Referring to FIG. 21, a further alternative embodiment of apparatus in accordance with the present invention is described. Catheter 440 comprises two occlusive members that surround the ostium of treatment vessel T. In this embodiment, catheter 440 having proximal occlusive member 442 and distal occlusive member 444 is provided in a retracted state. A section of catheter between the occlusive members may comprise blood intake port 446, as illustrated, or a plurality of blood intake ports. Distal occlusive members 444 is deployed at a location distal to the ostium of treatment vessel T. Distal occlusive member 444 channels blood flow into lumen 448 of catheter 440, and blood travels in a direction downstream. Proximal occlusive member 442 then may be deployed within host vessel H at a location proximal to the ostium of treatment vessel T, to allow fluid communication between treatment vessel T and lumen 448 via intake port 446.

The pressure differential between downstream flow and the flow within the treatment vessel T may cause a venturi effect that allows manipulation of flow within treatment vessel T. For example, a lower downstream pressure, i.e., at the proximal end of catheter 440, relative to the pressure within treatment vessel T, may cause a reversal of flow within treatment vessel T.

Catheter 440 and intake port 446 are sized to permit interventional devices, e.g., a conventional angioplasty balloon, to be advanced to the site of stenosis S. The venturi effect controls the level of flow within treatment vessel T throughout the procedure, and emboli E that are generated may be removed via intake port 446.

While preferred illustrative embodiments of the present invention are described above, it will be apparent to one skilled in the art that various changes and modifications may be made without departing from the invention. The appended claims are intended to cover all such changes and modifications that fall within the true spirit and scope of the invention.

What is claimed is:

1. Apparatus for removing emboli from a blood vessel, the apparatus comprising:

a catheter having a proximal end, a distal end, a blood outlet port at the proximal end, a distal inlet port at the distal end, a lateral surface, and a lumen extending between the proximal and distal ends;

an occlusive member affixed to the distal end of the catheter at a location proximal of the distal inlet port; and at least one intake port disposed in the lateral surface proximal to the occlusive member, the blood intake port configured to induce venturi-assisted retrograde flow in a treatment vessel so that blood entering the lumen flows from the distal inlet port to the blood outlet port.

2. The apparatus of claim 1 wherein the occlusive member is inflatable and includes a tapered surface that communicates with the lumen.

3. The apparatus of claim 2 wherein the occlusive member is adapted to be disposed within the ostium of a treatment vessel.

4. The apparatus of claim 2 wherein the occlusive member further serves as an inflatable cuff.

5. The apparatus of claim 1 wherein the occlusive member comprises a self-expanding woven mesh having contracted a state suitable for transluminal insertion and an expanded state suitable for occluding antegrade flow in a treatment vessel.

6. The apparatus of claim 5 wherein the occlusive member has a rounded configuration and an internal lip.

7. The apparatus of claim 5 wherein the occlusive member comprises a plurality of split ends coated with an elastomeric coating.

8. The apparatus of claim 1 further comprising:

a piston disposed for longitudinal motion within the catheter; and a flexible sheath affixed at a distal location to the piston and affixed at a proximal location to the catheter, so that proximally retracting the piston within the catheter causes the flexible sheath to form a balloon-shaped occlusive member.

9. The apparatus of claim 1 wherein the blood intake port has edges having variable angle configurations.

10. The apparatus of claim 1 wherein the blood intake port is disposed at an angle with respect to the catheter body.

11. The apparatus of claim 1 wherein the blood intake port has a pattern selected to enhance blood flow into the blood intake ports.

12. The apparatus of claim 1 wherein the catheter further comprises at least one deployable section, the deployable section having an expandable state wherein the proximal edges of the blood intake ports are raised with respect to the catheter body.

13. The apparatus of claim 1 wherein the blood intake port is circular.

14. The apparatus of claim 1 wherein the blood intake port is a slot.

15. The apparatus of claim 1 wherein the catheter further comprises a flexing member that separates a distal catheter section comprising the distal occlusive member and a proximal section comprising the blood intake port.

16. The apparatus of claim 15 further comprising a shape memory member having an expanded state suitable for bending the flexing member to form a substantially acute angle between the proximal and distal sections.

17. The apparatus of claim 1 further comprising:

an outer sheath; and a hood, the hood being provided in a contracted state within the outer sheath and having an expanded state suitable for guiding blood flow into the blood intake port.

18. A method for removing emboli during a medical procedure and manipulating flow characteristics in a treatment vessel, the method comprising:

providing apparatus comprising a catheter having a proximal end, a distal end, a blood outlet port at the proximal end, an inlet port at the distal end, a lumen extending therethrough, an occlusive member affixed to the distal end at a location proximal of the distal end, and at least one blood intake port disposed in a lateral surface of the catheter;

positioning the distal end of the catheter in a host vessel so that the inlet port extends in at least an ostium of the treatment vessel proximal to a stenosis; and deploying the occlusive member to prevent communication between the host and treatment vessels, such that a distal portion of the lumen communicates with flow in the treatment vessel; and flowing blood into the intake port so as to induce retrograde flow in the treatment vessel and cause blood entering the lumen through the inlet port to flow to the blood outlet port.

19. The method of claim 18 wherein deploying the occlusive member further comprises:

providing a piston capable of longitudinally moving within the lumen of the catheter, and further providing a flexible sheath that is affixed at a distal location to the piston and affixed at a proximal location to the catheter; and proximally retracting the piston within the catheter to compress air within the sheath to form a balloon-shaped occlusive member.

20. The method of claim 18 wherein flowing blood into the intake port further comprises controlling fluid flow from a host vessel into the lumen of the catheter via the blood intake port.

21. The method of claim 20 wherein flowing blood into the intake port further comprises inducing venturi-assisted retrograde flow in the treatment vessel.

22. The method of claim 20 further comprising performing a medical procedure to treat a lesion in the treatment vessel.

23. The method of claim 22 further comprising directing emboli generated during the medical procedure into the lumen of the catheter.

24. The method of claim 22 wherein controlling fluid flow into the lumen further comprises:

providing an inner sheath having at least one opening within the catheter; and actuating the inner sheath to allow the opening to overlap a selected amount with the intake port.

25. The method of claim 24 wherein actuating the inner sheath comprises rotating the inner sheath within the catheter relative to its longitudinal axis.

26. The method of claim 24 wherein actuating the inner sheath comprises longitudinally sliding the inner sheath within the catheter.

27. The method of claim 20 wherein controlling fluid flow into the lumen further comprises:

providing a flexing member positioned proximal to the occlusive member, the blood intake port positioned proximal to the flexing member, and a shape memory member that is initially retracted;

deploying the shape memory member to flex the flexing member to provide a substantially acute angle between the occlusive member and the intake port; and deploying the occlusive member proximal to a stenosis in a treatment vessel to anchor the distal end of the catheter.

28. The method of claim 27 further comprising proximally retracting a tensioning member affixed to a distal point within the lumen to bend the flexing member to increase the substantially acute angle.

* * * * *

UNITED STATES PATENT AND TRADEMARK OFFICE
CERTIFICATE OF CORRECTION

PATENT NO.    : 6,682,505 B2
DATED         : January 27, 2004
INVENTOR(S)   : Bates et al.

It is certified that error appears in the above-identified patent and that said Letters Patent is hereby corrected as shown below:

Delete Title page illustrating figure and substitute therefore new Title page illustrating figure (attached)

Delete drawing sheets 1-15 and substitute therefore drawing sheets 1-16 as shown on the attached sheet.

Signed and Sealed this

Fourteenth Day of September, 2004

JON W. DUDAS
*Director of the United States Patent and Trademark Office*

United States Patent
Bates et al.

(10) Patent No.: US 6,682,505 B2
(45) Date of Patent: Jan. 27, 2004

(54) CATHETER FOR REMOVING EMBOLI FROM SAPHENOUS VEIN GRAFTS AND NATIVE CORONARY ARTERIES

(75) Inventors: Mark C. Bates, Charleston, WV (US); Michael Hogendijk, Palo Alto, CA (US); Ryan P. Boucher, San Francisco, CA (US)

(73) Assignee: Arteria Medical Science, Inc., San Francisco, CA (US)

(*) Notice: Subject to any disclaimer, the term of this patent is extended or adjusted under 35 U.S.C. 154(b) by 0 days.

(21) Appl. No.: 09/909,729

(22) Filed: Jul. 19, 2001

(65) Prior Publication Data
US 2002/0107479 A1 Aug. 8, 2002

Related U.S. Application Data

(63) Continuation-in-part of application No. 09/418,727, filed on Oct. 15, 1999, now Pat. No. 6,423,032, which is a continuation-in-part of application No. 09/333,074, filed on Jun. 14, 1999, now Pat. No. 6,206,868.

(30) Foreign Application Priority Data

Mar. 12, 1999 (WO) .................. PCT/US99/05469

(51) Int. Cl.$^7$ ................................ A61M 29/00
(52) U.S. Cl. ................... 604/96.01; 604/103.07
(58) Field of Search ............... 604/96.01, 915–920; 606/191–194

(56) References Cited

U.S. PATENT DOCUMENTS

| | | |
|---|---|---|
| 4,575,371 A | 3/1986 | Nordqvist et al. |
| 4,781,681 A | 11/1988 | Sharrow et al. |
| 4,794,928 A | 1/1989 | Kletschka |
| 4,921,478 A | 5/1990 | Solano et al. |
| 5,011,488 A | 4/1991 | Ginsburg |
| 5,102,415 A | 4/1992 | Guenther et al. |
| 5,284,473 A * | 2/1994 | Calabria .................. 604/53 |
| 5,549,626 A | 8/1996 | Miller et al. |
| 5,584,803 A | 12/1996 | Stevens et al. |
| 5,669,927 A | 9/1997 | Boebel et al. |
| 5,749,858 A | 5/1998 | Cramer |
| 5,766,151 A | 6/1998 | Valley et al. |
| 5,794,629 A | 8/1998 | Frazee |
| 5,833,650 A | 11/1998 | Imran |
| 5,895,399 A | 4/1999 | Barbut et al. |
| 5,916,193 A | 6/1999 | Stevens et al. |
| 5,938,645 A | 8/1999 | Gordon |
| 5,997,557 A | 12/1999 | Barbut et al. |
| 6,013,085 A | 1/2000 | Howard |
| 6,027,476 A | 2/2000 | Sterman et al. |
| 6,029,671 A | 2/2000 | Stevens et al. |
| 6,042,559 A | 3/2000 | Dobak, III |
| 6,161,547 A | 12/2000 | Barbut |
| 6,165,199 A | 12/2000 | Barbut |
| 6,180,059 B1 | 1/2001 | Divino et al. |
| 6,228,052 B1 | 5/2001 | Pohndorf |
| 6,295,989 B1 | 10/2001 | Connors, III |
| 6,398,773 B1 * | 6/2002 | Bagaoisan et al. .......... 604/509 |
| 6,454,741 B1 * | 9/2002 | Muni et al. ............... 604/96.01 |

FOREIGN PATENT DOCUMENTS

EP   0 427 429 A2   5/1991

* cited by examiner

Primary Examiner—Manuel Mendez
(74) Attorney, Agent, or Firm—Luce, Forward, Hamilton & Scripps; Nicole A. Pisano

(57) ABSTRACT

Methods and apparatus are provided for removing emboli generated during a surgical procedure comprising a catheter having proximal and distal ends, a lumen extending therethrough, an occlusive member affixed to the distal end, and at least one blood intake port disposed in a lateral surface of the catheter. The occlusive member preferably is disposed in a treatment vessel, and the blood intake port, when uncovered, permits a portion of the antegrade flow from a host vessel to be diverted into the lumen of the catheter. A pressure differential caused by the blood intake from the host vessel establishes a venturi-effect suitable for manipulating flow in the treatment vessel. The flow characteristics may be manipulated via the intake port to direct emboli into the lumen of the catheter for subsequent removal.

28 Claims, 15 Drawing Sheets

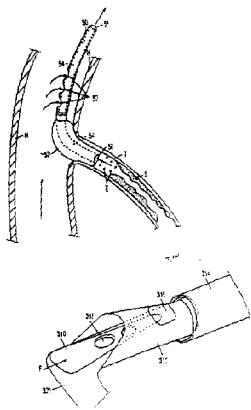

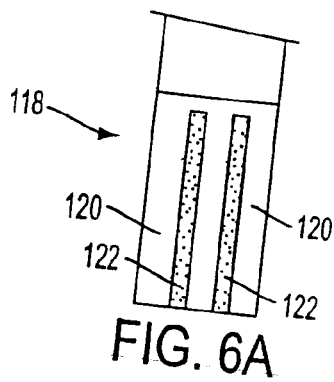
FIG. 6A
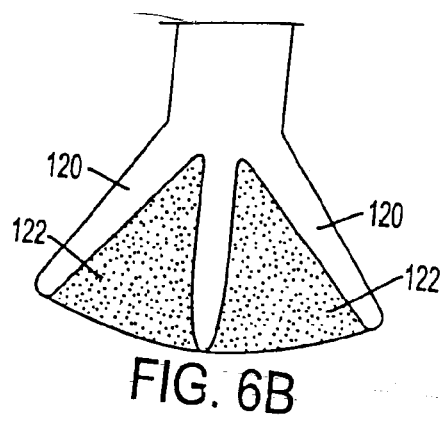
FIG. 6B
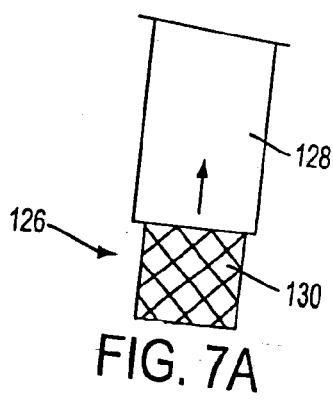
FIG. 7A
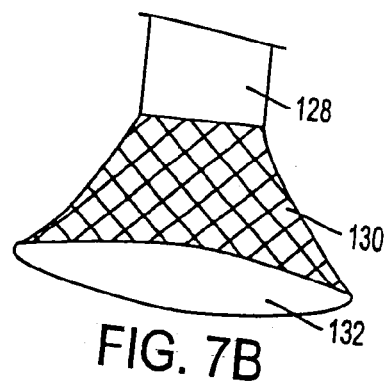
FIG. 7B
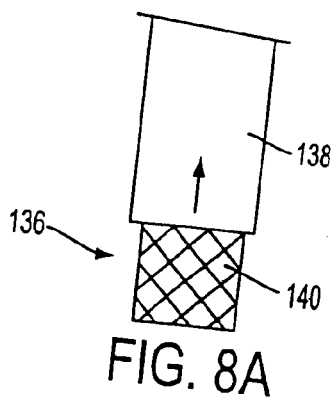
FIG. 8A
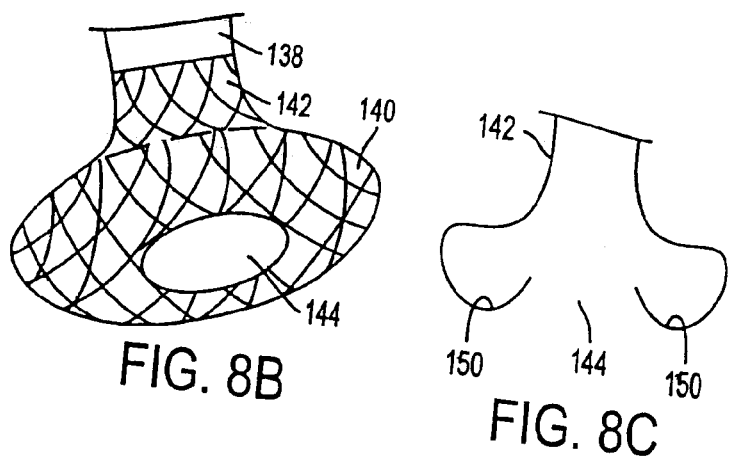
FIG. 8B
FIG. 8C